US012198371B2

(12) United States Patent
Endo

(10) Patent No.: US 12,198,371 B2
(45) Date of Patent: Jan. 14, 2025

(54) MEDICAL IMAGE PROCESSING APPARATUS, PROCESSOR DEVICE, MEDICAL IMAGE PROCESSING METHOD, AND PROGRAM

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 670 days.

(21) Appl. No.: 17/199,470

(22) Filed: Mar. 12, 2021

(65) Prior Publication Data

US 2021/0196099 A1 Jul. 1, 2021

Related U.S. Application Data

(63) Continuation of application No. PCT/JP2019/035054, filed on Sep. 5, 2019.

(30) Foreign Application Priority Data

Sep. 18, 2018 (JP) ................................. 2018-173991

(51) Int. Cl.
*G06T 7/73* (2017.01)
*G06T 7/00* (2017.01)
(Continued)

(52) U.S. Cl.
CPC .............. *G06T 7/73* (2017.01); *G06T 7/0012* (2013.01); *G06V 10/25* (2022.01); *A61B 1/000094* (2022.02); *G06T 2207/10068* (2013.01)

(58) Field of Classification Search
CPC .......... A61B 1/000094; A61B 1/00009; A61B 1/000095; A61B 1/00055; G06T 7/73;
(Continued)

(56) References Cited

U.S. PATENT DOCUMENTS 8,282,551 B2 10/2012 Satoh
11,426,054 B2 * 8/2022 Shigeta ................ A61B 1/0005
(Continued)

FOREIGN PATENT DOCUMENTS

CN 108135457 6/2018
JP 2007306416 11/2007
(Continued)

OTHER PUBLICATIONS

Office Action of Japan Counterpart Application, with English translation thereof, issued on May 13, 2022, pp. 1-6.
(Continued)

*Primary Examiner* — Brian P Yenke
(74) *Attorney, Agent, or Firm* — JCIPRNET

(57) ABSTRACT

Provided are a medical image processing apparatus, a processor device, a medical image processing method, and a program that may suppress flickering of display when a region of interest in a medical image is reported. A medical image processing apparatus includes an image acquisition unit (40) that acquires an endoscopic image (38), a region-of-interest detection unit (41) that detects a region of interest, an emphasis region setting unit (42) that sets a location of an emphasis region for emphasizing the region of interest in accordance with a location of the region of interest when the medical image is displayed using a monitor device (16), and a display control unit (44) that updates display of the emphasis region using an update interval exceeding an update interval of display of the endoscopic image.

15 Claims, 12 Drawing Sheets

(51) Int. Cl.
*G06V 10/25* (2022.01)
*A61B 1/00* (2006.01)

(58) Field of Classification Search
CPC ........ G06T 7/0012; G06T 2207/10068; G06V 10/25

See application file for complete search history.

(56) References Cited

U.S. PATENT DOCUMENTS

| | | | |
|---|---|---|---|
| 11,464,394 B2 * | 10/2022 | Endo | A61B 1/000096 |
| 11,471,123 B2 * | 10/2022 | Maeda | A61B 8/0883 |
| 11,477,370 B2 * | 10/2022 | Schröer | A61B 1/00045 |
| 11,910,994 B2 * | 2/2024 | Takenouchi | A61B 1/0005 |
| 12,059,123 B2 * | 8/2024 | Kamon | A61B 1/000094 |
| 2007/0266312 A1 | 11/2007 | Ayaki et al. | |
| 2012/0259225 A1 * | 10/2012 | Tashiro | A61B 8/469 600/443 |
| 2012/0274754 A1 * | 11/2012 | Tsuruoka | A61B 1/0638 348/222.1 |
| 2015/0080712 A1 | 3/2015 | Van Keersop et al. | |
| 2015/0103208 A1 * | 4/2015 | Tsuchida | H04N 5/272 348/239 |
| 2015/0327825 A1 * | 11/2015 | Suzuki | A61B 6/542 378/4 |
| 2017/0209122 A1 * | 7/2017 | Lee | A61B 8/469 |
| 2017/0345268 A1 * | 11/2017 | Cho | G08B 13/19673 |
| 2018/0242817 A1 | 8/2018 | Imaizumi et al. | |
| 2018/0307933 A1 * | 10/2018 | Iwaki | A61B 1/000094 |
| 2019/0069757 A1 * | 3/2019 | Iwaki | G06T 7/70 |
| 2019/0099060 A1 * | 4/2019 | Yaguchi | G06T 7/0012 |
| 2019/0239718 A1 * | 8/2019 | Iwaki | G02B 23/2461 |
| 2019/0290247 A1 * | 9/2019 | Popovic | A61B 1/0005 |
| 2020/0058124 A1 * | 2/2020 | Iwaki | G06T 7/0012 |
| 2020/0069160 A1 * | 3/2020 | Oosake | A61B 1/00045 |
| 2021/0082568 A1 * | 3/2021 | Kamon | G16H 50/20 |
| 2021/0113159 A1 * | 4/2021 | Kono | G06T 11/00 |
| 2021/0158520 A1 * | 5/2021 | Kamon | A61B 1/00045 |
| 2021/0174115 A1 * | 6/2021 | Kamon | G06F 18/213 |
| 2021/0201486 A1 * | 7/2021 | Takenouchi | A61B 1/0005 |
| 2021/0204794 A1 * | 7/2021 | Yumbe | G09G 5/377 |
| 2021/0327037 A1 * | 10/2021 | Hares | A61B 34/30 |
| 2021/0342592 A1 * | 11/2021 | Oosake | G06T 7/0012 |
| 2021/0366110 A1 * | 11/2021 | Oosake | A61B 1/000094 |
| 2022/0151467 A1 * | 5/2022 | Meguro | A61B 1/000096 |
| 2023/0027950 A1 * | 1/2023 | Endo | A61B 90/361 |
| 2024/0153090 A1 * | 5/2024 | Saikou | G16H 30/40 |

FOREIGN PATENT DOCUMENTS

| | | |
|---|---|---|
| JP | 2011255006 | 12/2011 |
| JP | 4897460 | 3/2012 |
| WO | 2017203560 | 11/2017 |
| WO | 2017212653 | 12/2017 |

OTHER PUBLICATIONS

"Search Report of Europe Counterpart Application", issued on Oct. 22, 2021, p. 1-p. 7.

"International Search Report (Form PCT/ISA/210) of PCT/JP2019/035054," mailed on Dec. 3, 2019, with English translation thereof, pp. 1-3.

"Written Opinion of the International Searching Authority (Form PCT/ISA/237) of PCT/JP2019/035054," mailed on Dec. 3, 2019, with English translation thereof, pp. 1-12.

"Office Action of China Counterpart Application", issued on Jun. 1, 2024, with English translation thereof, pp. 1-9.

"Office Action of China Counterpart Application", issued on Nov. 24, 2023, with English translation thereof, p. 1-p. 15.

Office Action of Europe Counterpart Application, issued on Dec. 6, 2023, p. 1-p. 4.

* cited by examiner

MEDICAL IMAGE PROCESSING APPARATUS, PROCESSOR DEVICE, MEDICAL IMAGE PROCESSING METHOD, AND PROGRAM

CROSS-REFERENCE TO RELATED APPLICATIONS

The present application is a Continuation of PCT International Application No. PCT/JP2019/035054 filed on Sep. 5, 2019 claiming priority under 35 U.S.C § 119(a) to Japanese Patent Application No. 2018-173991 filed on Sep. 18, 2018. Each of the above applications is hereby expressly incorporated by reference, in its entirety, into the present application.

BACKGROUND OF THE INVENTION

Field of the Invention

The present invention relates to a medical image processing apparatus, a processor device, a medical image processing method, and a program, and more particularly to reporting of a detection result.

Description of the Related Art

JP4897460B describes an ultrasound image diagnostic apparatus that sets a region of interest on the basis of an ultrasound image, performs speckle analysis on a desired site of a subject, and displays the ultrasound image and a speckle analysis result in real time.

The apparatus described in JP4897460B is capable of setting an update rate of the speckle analysis result against an issue that a high frame rate of the ultrasound image makes it difficult to read the speckle analysis result when the speckle analysis result is displayed in a live mode. This enables the speckle analysis result to be read even at a high frame rate of the ultrasound image.

JP2011-255006A describes an image processing apparatus that determines whether to display an alert image corresponding to a region of interest in accordance with a detection result of the region of interest, and displays the alert image corresponding to the display-target region of interest that is a region of interest for which the alert image is determined to be displayed.

According to the invention described in JP2011-255006A, when the number of regions of interest is small, an alert image is not displayed for a region of interest having a size exceeding a threshold value. When the number of regions of interest is large, an alert image is not displayed for a region of interest having a size smaller than or equal to the threshold value.

SUMMARY OF THE INVENTION

A medical diagnostic system for automatically detecting a lesion portion has an issue that, since a detected location of a lesion constantly changes, flickering occurs in a report portion for reporting the location of the lesion when the detection result is displayed on a monitor and hinders diagnosis.

The invention described in JP4897460B enables adjustment of the update rate of the speckle analysis result. However, the invention does not focus on the issue of flickering that occurs when the speckle analysis result is displayed and includes no constituent element for addressing the issue.

The invention described in JP2011-255006A switches between display and non-display of an alert image. However, the invention does not focus on the issue of flickering that occurs when the alert image is displayed and includes no constituent element for addressing the issue.

The present invention is made in view of such circumstances, and an object thereof is to provide a medical image processing apparatus, a processor device, a medical image processing method, and a program that may suppress flickering that occurs when a region of interest in a medical image is reported.

In order to achieve the above object, the following aspects of the invention are provided.

A medical image processing apparatus according to a first aspect is a medical image processing apparatus including an image acquisition unit that acquires a medical image, a region-of-interest detection unit that detects a region of interest from the medical image, an emphasis region setting unit that sets a location of an emphasis region for emphasizing the region of interest in accordance with a location of the region of interest when the medical image is displayed using a display device, and a display control unit that updates display of the emphasis region using an update interval exceeding an update interval of display of the medical image.

According to the first aspect, the display timing for updating the display of the emphasis region is controlled using the update interval exceeding the update interval of the display of the medical image. Thus, the location of the emphasis region is updated with a delay with respect to the update of the display of the medical image. Consequently, flickering may be suppressed when the region of interest in the medical image is reported and visibility may be improved when a user visually recognizes the region of interest.

In a second aspect, the medical image processing apparatus according to the first aspect may further include an update interval setting unit that sets the update interval of the emphasis region.

In a third aspect, the medical image processing apparatus according to the second aspect may further include a signal reception unit that receives a signal indicating the update interval of the emphasis region, the signal being transmitted from outside, in which the update interval setting unit may set the update interval of the emphasis region on the basis of the signal indicating the update interval of the emphasis region received using the signal reception unit.

In a fourth aspect, in the medical image processing apparatus according to the second or third aspect, the update interval setting unit may set the update interval of the emphasis region in accordance with a movement of an imaging apparatus that acquires the medical image.

In a fifth aspect, in the medical image processing apparatus according to any one of the second to fourth aspects, the update interval setting unit may set the update interval of the emphasis region in accordance with a discrimination result of the region of interest.

In a sixth aspect, in the medical image processing apparatus according to any one of the first to fifth aspects, the display control unit may cause the display device to display the emphasis region while maintaining, for a period from an update timing of the display of the emphasis region to a next update timing of the display of the emphasis region, the location of the emphasis region set at the update timing of the display of the emphasis region.

In a seventh aspect, in the medical image processing apparatus according to any one of the first to sixth aspects, the display control unit may transmit, to the display device, a signal for displaying the emphasis region, set using the emphasis region setting unit, to be superimposed on the medical image.

In an eighth aspect, in the medical image processing apparatus according to any one of the first to seventh aspects, the emphasis region setting unit may set the location of the emphasis region in a frame at an update timing of the emphasis region on the basis of locations of the regions of interest in two or more frames preceding the frame at the update timing of the emphasis region.

In a ninth aspect, in the medical image processing apparatus according to the eighth aspect, the emphasis region setting unit may set the location of the emphasis region in the frame at the update timing of the emphasis region on the basis of an average of the locations of the regions of interest in the two or more frames preceding the frame at the update timing of the emphasis region.

In a tenth aspect, in the medical image processing apparatus according to any one of the first to ninth aspects, at an update timing of the display of the emphasis region, the emphasis region setting unit may set an emphasis region obtained by merging an emphasis region in a past frame with the emphasis region at the update timing of the display of the emphasis region.

A processor device according to an eleventh aspect is a processor device including an endoscope control unit that controls an endoscope, an image acquisition unit that acquires a medical image from the endoscope, a region-of-interest detection unit that detects a region of interest from the medical image, an emphasis region setting unit that sets a location of an emphasis region for emphasizing the region of interest in accordance with a location of the region of interest when the medical image is displayed using a display device, and a display control unit that updates display of the emphasis region using an update interval exceeding an update interval of display of the medical image.

According to the eleventh aspect, substantially the same advantage as that of the first aspect can be obtained.

The eleventh aspect may be appropriately combined with substantially the same features as those specified in the second to tenth aspects. In such a case, a constituent element responsible for a process or function specified in the medical image processing apparatus can be grasped as a constituent element responsible for the corresponding process or function in the processor device.

A medical image processing method according to a twelfth aspect is a medical image processing method including an image acquisition step of acquiring a medical image, a region-of-interest detection step of detecting a region of interest from the medical image, an emphasis region setting step of setting a location of an emphasis region for emphasizing the region of interest in accordance with a location of the region of interest when the medical image is displayed using a display device, and a display control step of updating display of the emphasis region using an update interval exceeding an update interval of display of the medical image.

According to the twelfth aspect, substantially the same advantage as that of the first aspect can be obtained.

The twelfth aspect may be appropriately combined with substantially the same features as those specified in the second to tenth aspects. In such a case, a constituent element responsible for a process or function specified in the medical image processing apparatus can be grasped as a constituent element responsible for the corresponding process or function in the medical image processing method.

A program according to a thirteenth aspect is a program that causes a computer to implement an image acquisition function of acquiring a medical image, a region-of-interest detection function of detecting a region of interest from the medical image, an emphasis region setting function of setting a location of an emphasis region for emphasizing the region of interest in accordance with a location of the region of interest when the medical image is displayed using a display device, and a display control function of updating display of the emphasis region using an update interval exceeding an update interval of display of the medical image.

According to the thirteenth aspect, substantially the same advantage as that of the first aspect can be obtained.

The thirteenth aspect may be appropriately combined with substantially the same features as those specified in the second to tenth aspects. In such a case, a constituent element responsible for a process or function specified in the medical image processing apparatus can be grasped as a constituent element responsible for the corresponding process or function in the program.

According to the present invention, a display timing for updating display of an emphasis region is controlled using an update interval exceeding an update interval of display of a medical image. Thus, the location of the emphasis region is updated with a delay with respect to update of the display of the medical image. Consequently, flickering may be suppressed when a region of interest in the medical image is reported and visibility may be improved when a user visually recognizes the region of interest.

DESCRIPTION OF THE PREFERRED EMBODIMENTS

Preferred embodiments of the present invention will be described in detail below with reference to the accompanying drawings. The same constituent elements are denoted by the same reference signs herein, and redundant description will be appropriately omitted.

Overall Configuration of Endoscope System

Figure 1:
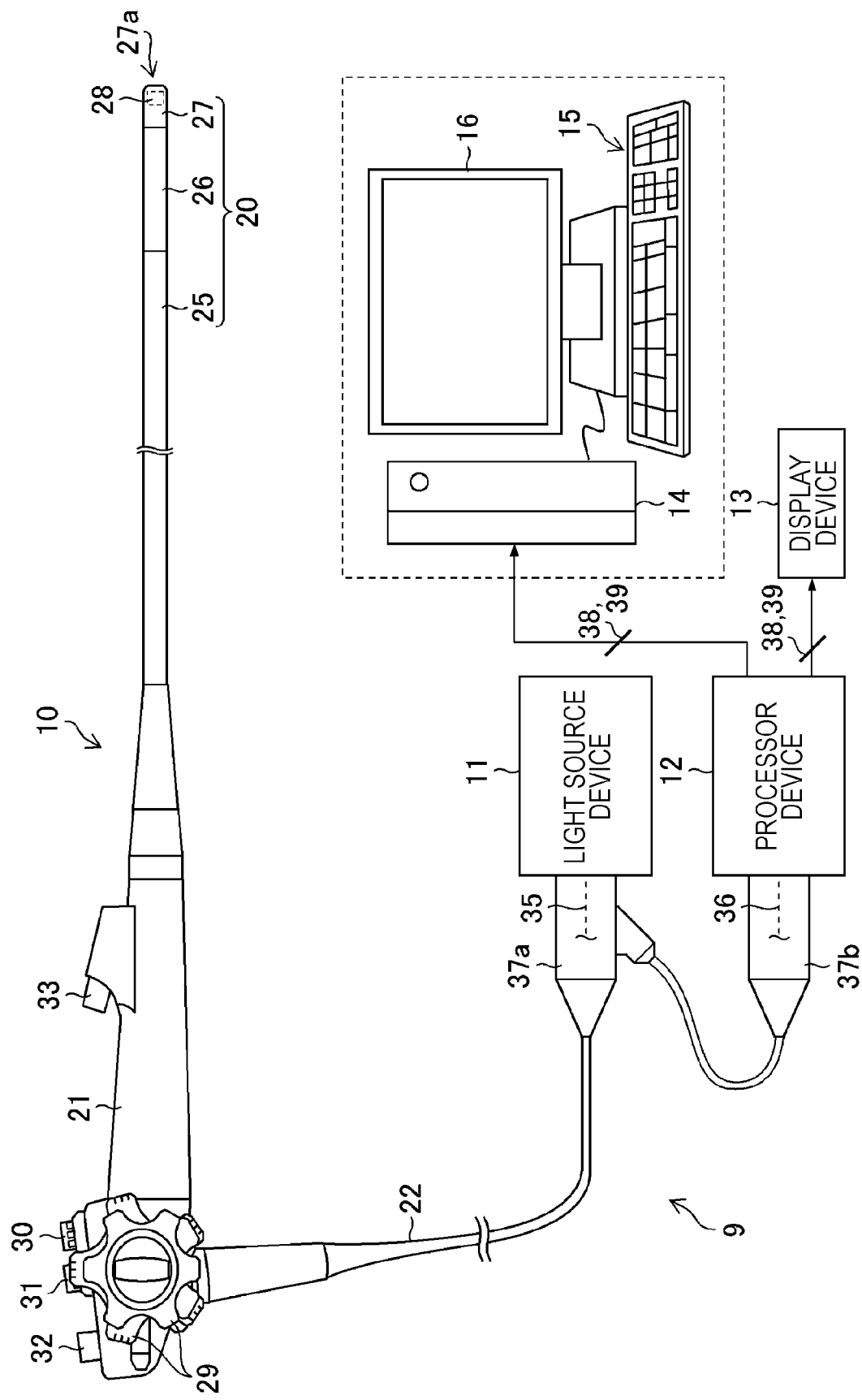
FIG. 1 is an overall configuration diagram of an endoscope system including a medical image processing apparatus according to an embodiment.

FIG. 1 is an overall configuration diagram of an endoscope system including a medical image processing apparatus according to embodiments. An endoscope system 9 illustrated in FIG. 1 includes an endoscope 10, a light source device 11, a processor device 12, a display device 13, a medical image processing apparatus 14, an input device 15, and a monitor device 16.

The endoscope 10 illustrated in FIG. 1 is an electronic endoscope and is also a flexible endoscope. The endoscope 10 includes an insertion section 20, an operation section 21, and a universal cord 22. The insertion section 20 is inserted into a subject. The entire insertion section 20 is formed to have an elongated shape with a small diameter.

The insertion section 20 includes a soft part 25, a bending part 26, and a tip part 27. The soft part 25, the bending part 26, and the tip part 27 are coupled to each other to constitute the insertion section 20. The soft part 25 has flexibility and bends sequentially from a proximal end side to a distal end side of the insertion section 20. The bending part 26 has a structure that is bendable when the operation section 21 is operated. The tip part 27 includes an imaging optical system (not illustrated), an imaging element 28, and so on.

A CMOS imaging element or a CCD imaging element is used as the imaging element 28. CMOS is an abbreviation for complementary metal oxide semiconductor. CCD is an abbreviation for charge coupled device.

An observation window (not illustrated) is disposed on a tip surface 27a of the tip part 27. The observation window is an opening formed on the tip surface 27a of the tip part 27. A cover (not illustrated) is attached to the observation window. The imaging optical system (not illustrated) is disposed behind the observation window. Image light of a site to be observed is incident onto an imaging surface of the imaging element 28 through the observation window, the imaging optical system, and so on. The imaging element 28 images the image light of the site to be observed incident onto the imaging surface of the imaging element 28 and outputs an imaging signal. The term "imaging" used herein includes the meaning of converting light reflected off from a site to be observed into an electric signal.

The operation section 21 is coupled to the proximal end side of the insertion section 20. The operation section 21 includes various operating members to be operated by a technician. Specifically, the operation section 21 includes two types of bending operation knobs 29. The bending operation knobs 29 are used to perform an operation of bending the bending part 26. Note that the technician may also be referred to as a doctor, an operator, an observer, a user, or the like.

The operation section 21 includes an air/water supply button 30 and a suction button 31. The air/water supply button 30 is used when the technician performs an air/water supply operation. The suction button 31 is used when the technician performs a suction operation.

Figure 3:
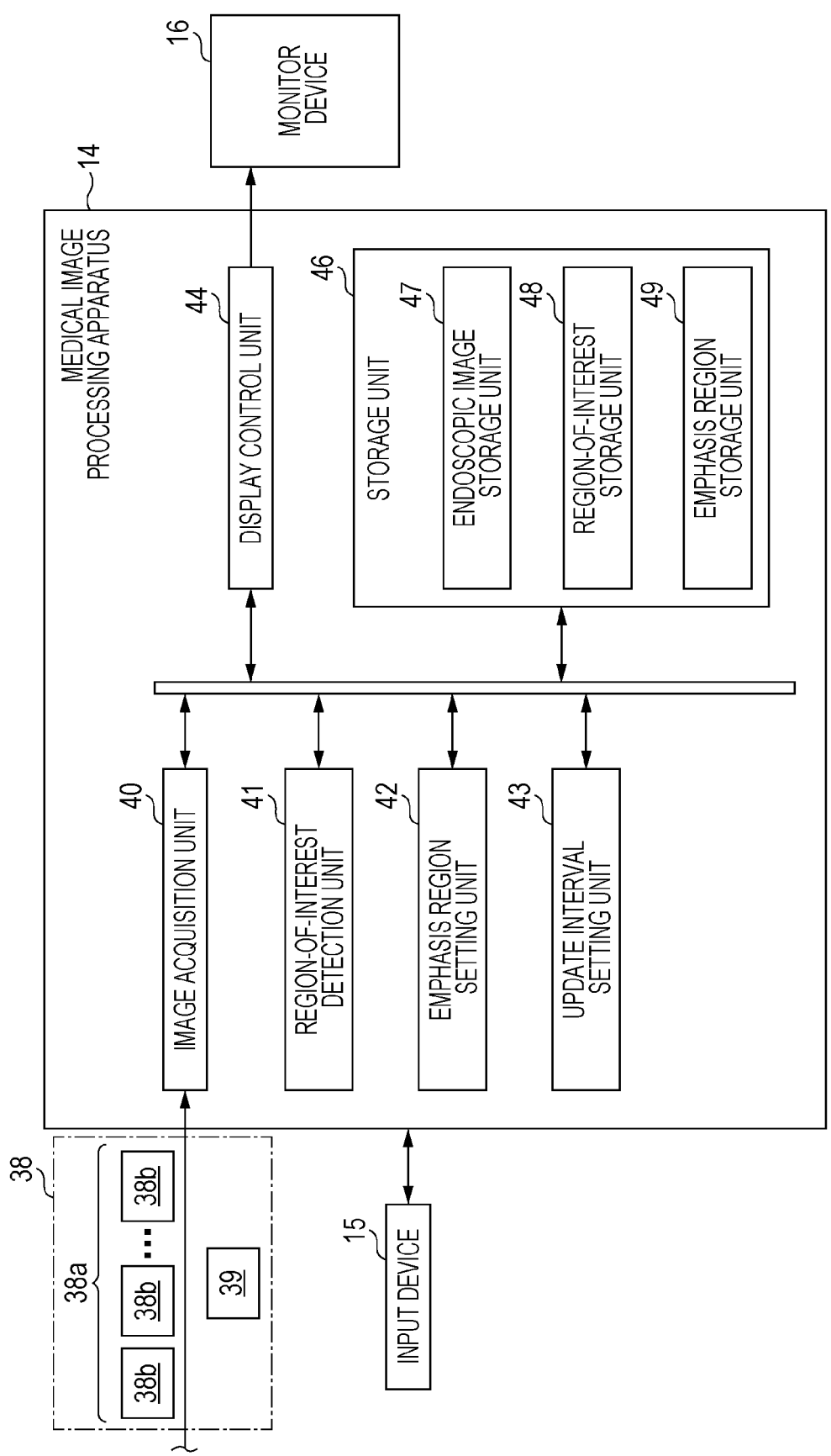
FIG. 3 is a functional block diagram of the medical image processing apparatus according to a first embodiment.

The operation section 21 includes a still image capturing instruction part 32 and a treatment tool introduction port 33. The still image capturing instruction part 32 is operated by the technician when a still image of the site to be observed is captured. The treatment tool introduction port 33 is an opening through which a treatment tool is to be inserted into a treatment tool insertion path that is inserted inside the insertion section 20. Note that illustration of the treatment tool insertion path and the treatment tool is omitted. A still image, assigned a reference sign 39, is illustrated in FIG. 3.

The universal cord 22 is a connection cord that connects the endoscope 10 to the light source device 11. The universal cord 22 includes therein a light guide 35, a signal cable 36, and a fluid tube (not illustrated), which are inserted inside the insertion section 20.

In addition, a tip part of the universal cord 22 includes a connector 37a to be connected to the light source device 11 and a connector 37b branching from the connector 37a and to be connected to the processor device 12.

When the connector 37a is connected to the light source device 11, the light guide 35 and the fluid tube (not illustrated) are inserted into the light source device 11. Consequently, necessary illumination light, water, and gas are supplied from the light source device 11 to the endoscope 10 through the light guide 35 and the fluid tube (not illustrated).

As a result, the illumination light is radiated from an illumination window (not illustrated) of the tip surface 27a of the tip part 27 toward the site to be observed. In addition, in response to an operation of pressing the air/water supply button 30, gas or water is ejected from an air/water supply nozzle (not illustrated) of the tip surface 27a of the tip part 27 toward the observation window (not illustrated) of the tip surface 27a.

When the connector 37b is connected to the processor device 12, the signal cable 36 and the processor device 12 are electrically connected to each other. Consequently, an imaging signal of the site to be observed is output from the imaging element 28 of the endoscope 10 to the processor device 12 through the signal cable 36. Also, a control signal is output from the processor device 12 to the endoscope 10 through the signal cable 36.

In the present embodiments, the flexible endoscope is described as an example of the endoscope 10. However, various types of electronic endoscopes capable of capturing a moving image of a site to be observed, such as a rigid endoscope, may be used as the endoscope 10.

The light source device 11 supplies illumination light to the light guide 35 of the endoscope 10 through the connector 37a. White light or light in a specific wavelength range is usable as the illumination light. The illumination light may be a combination of white light and light in a specific wavelength range. The light source device 11 is configured to be able to appropriately select, as the illumination light, light in a wavelength range corresponding to an observation purpose.

The white light may be light in a white wavelength range or light in a plurality of wavelength ranges. The specific wavelength range is a range narrower than the white wavelength range. As the light in the specific wavelength range, light in a single wavelength range may be used, or light in a plurality of wavelength ranges may be used. Light in the specific wavelength range may be referred to as special light.

The processor device 12 controls the operation of the endoscope 10 through the connector 37b and the signal cable 36. The processor device 12 also acquires an imaging signal from the imaging element 28 of the endoscope 10 through the connector 37b and the signal cable 36. The processor device 12 uses a predetermined frame rate to acquire an imaging signal output from the endoscope 10.

The processor device 12 generates an endoscopic image 38, which is an observation image of the site to be observed, on the basis of the imaging signal acquired from the endoscope 10. Herein, the endoscopic image 38 includes a moving image. The endoscopic image 38 may include a still image 39. Note that a moving image, assigned a reference sign 38a, is illustrated in FIG. 3.

When the still image capturing instruction part 32 of the operation section 21 is operated, the processor device 12 generates the still image 39 of the site to be observed on the basis of the imaging signal acquired from the imaging element 28 in parallel with generation of the moving image. The still image 39 may be generated to have a resolution higher than the resolution of the moving image.

When the endoscopic image 38 is generated, the processor device 12 performs image quality correction in which digital signal processing such as white balance adjustment and shading correction are used. The processor device 12 may add accessory information defined by the DICOM standard to the endoscopic image 38. Note that DICOM is an abbreviation for Digital Imaging and Communications in Medicine. The processor device 12 described in the embodiments is an example of a processor device including an endoscope control unit that controls an endoscope.

The processor device 12 outputs the endoscopic image 38 to each of the display device 13 and the medical image processing apparatus 14. The processor device 12 may output the endoscopic image 38 to a storage device (not illustrated) via a network (not illustrated) in accordance with a communication protocol compliant with the DICOM standard. A network 140 illustrated in FIG. 2 may be used as the network.

The display device 13 is connected to the processor device 12. The display device 13 displays the endoscopic image 38 on the basis of the signal transmitted from the processor device 12. The technician may perform an operation of moving the insertion section 20 forward and backward while checking the endoscopic image 38 displayed on the display device 13. Upon detecting a lesion or the like at the site to be observed, the technician may operate the still image capturing instruction part 32 to capture a still image of the site to be observed.

A computer is used as the medical image processing apparatus 14. A keyboard, a mouse, and the like connectable to the computer are used as the input device 15. The input device 15 and the computer may be connected to each other either with a cable or wirelessly. Various monitors connectable to the computer are used as the monitor device 16.

As the medical image processing apparatus 14, a diagnosis assistant apparatus such as a workstation or a server apparatus may be used. In this case, the input device 15 and the monitor device 16 are provided for each of a plurality of terminals connected to the workstation or the like. Further, as the medical image processing apparatus 14, a medical service assistant apparatus that assists creation of a medical report or the like may be used.

The medical image processing apparatus 14 acquires the endoscopic image 38 and stores the endoscopic image 38. The medical image processing apparatus 14 controls reproduction performed by the monitor device 16. Note that the term "image" used herein includes the meaning of an electric signal representing the image and a meaning of image data such as information representing the image. That is, the term "image" used herein means at least any of an image itself or image data.

The term "storing an image" is replaceable with "saving an image" or "storage of an image". "Storing an image" used herein means "storing an image in a non-transitory manner". The medical image processing apparatus 14 may include a temporary storage memory that temporarily stores an image.

The input device 15 is used to input an operation instruction for the medical image processing apparatus 14. The monitor device 16 displays the endoscopic image 38 under the control of the medical image processing apparatus 14. The monitor device 16 may function as a display unit of various kinds of information in the medical image processing apparatus 14.

The medical image processing apparatus 14 may be connected to a storage device (not illustrated) via a network (not illustrated in FIG. 1). The DICOM standard, a protocol compliant with the DICOM standard, and the like may be used as the image storage format and for the communication between apparatuses via the network.

As the storage device (not illustrated), a storage or the like that stores data in a non-transitory manner may be used. The storage device may be managed using a server apparatus (not illustrated). As the server apparatus, a computer that stores and manages various kinds of data may be used.

Hardware Configuration of Medical Image Processing Apparatus

Figure 2:
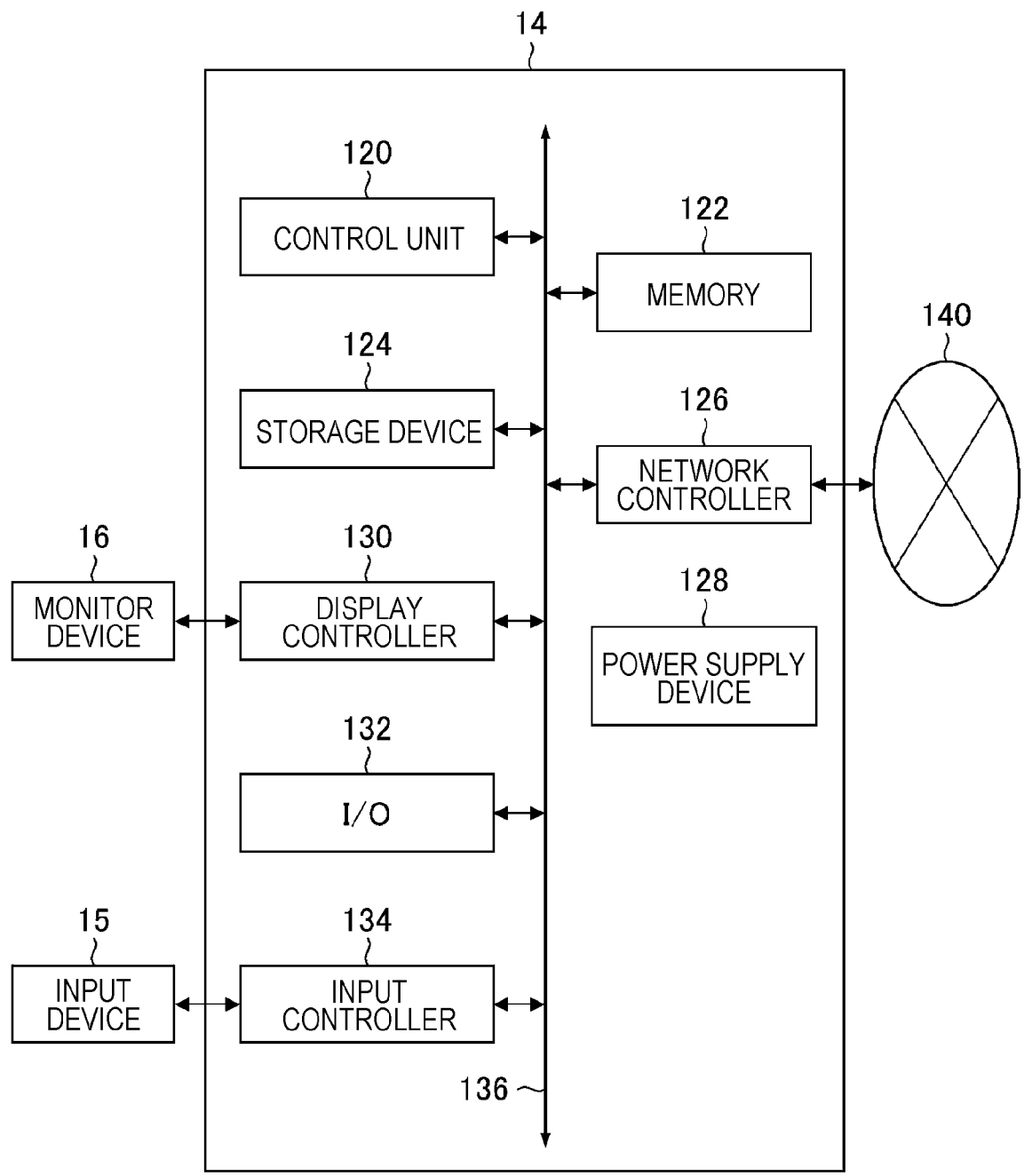
FIG. 2 is a block diagram illustrating a hardware configuration of the medical image processing apparatus.

FIG. 2 is a block diagram illustrating a hardware configuration of the medical image processing apparatus. The medical image processing apparatus 14 illustrated in FIG. 2 includes a control unit 120, a memory 122, a storage device 124, a network controller 126, a power supply device 128, a display controller 130, an input/output interface 132, and an input controller 134. Note that I/O illustrated in FIG. 2 represents the input/output interface.

The control unit 120, the memory 122, the storage device 124, the network controller 126, the display controller 130, and the input/output interface 132 are connected to each other via a bus 136 so that data communication can be performed therebetween.

Control Unit

The control unit 120 functions as an overall control unit, various calculation units, and a storage control unit of the medical image processing apparatus 14. The control unit 120 executes a program stored in a read-only memory (ROM) included in the memory 122.

The control unit 120 may download a program from an external storage device (not illustrated) via the network controller 126 and execute the downloaded program. The external storage device may be communicably connected to the medical image processing apparatus 14 via the network 140.

The control unit 120 uses, as a calculation area, a random access memory (RAM) included in the memory 122 and executes various processes in cooperation with various programs. Consequently, various functions of the medical image processing apparatus 14 are implemented.

The control unit 120 controls reading out of data from the storage device 124 and writing of data to the storage device 124. The control unit 120 may acquire various kinds of data from an external storage device via the network controller 126. The control unit 120 is capable of executing various processes such as calculations using the acquired various kinds of data.

The control unit 120 may include one processor or two or more processors. Examples of the processor include a field programmable gate array (FPGA), a programmable logic device (PLD), and so on. An FPGA and a PLD are devices whose circuit configurations are changeable after being manufactured.

Another example of the processor is an application-specific integrated circuit (ASIC). An ASIC includes a circuit configuration dedicatedly designed to execute specific processing.

The control unit 120 may use two or more processors of the same kind. For example, the control unit 120 may use two or more FPGAs or two or more PLDs. The control unit 120 may use two or more processors of different kinds. For example, the control unit 120 may use one or more FPGAs and one or more ASICs.

When the medical image processing apparatus 14 includes a plurality of control units 120, the plurality of control units 120 may be configured using a single processor. As an example of configuring the plurality of control units 120 using a single processor, there is a form in which the single processor is configured using a combination of one or more central processing units (CPUs) and software and this processor functions as the plurality of control units 120. Note that software used herein is synonymous with a program.

As another example of configuring the plurality of control units 120 using a single processor, there is a form in which a processor that implements, with a single IC chip, the functions of the entire system including the plurality of control units 120. Representative examples of the processor that implements, with a single IC chip, the functions of the entire system including the plurality of control units 120 include a system on a chip (SoC). Note that IC is an abbreviation for integrated circuit.

As described above, the control unit 120 is configured using one or more of various kinds of processors as the hardware structure.

Memory

The memory 122 includes a ROM (not illustrated) and a RAM (not illustrated). The ROM stores various programs to be executed in the medical image processing apparatus 14. The ROM stores parameters, files, and the like used for executing various programs. The RAM functions as a temporary data storage area, a work area for the control unit 120, and the like.

Storage Device

The storage device 124 stores various kinds of data in a non-transitory manner. The storage device 124 may be externally attached to the medical image processing apparatus 14. Instead of or along with the storage device 124, a large-capacity semiconductor memory device may be used.

Network Controller

The network controller 126 controls data communication between the medical image processing apparatus 14 and an external apparatus. The control of the data communication may include management of the traffic in the data communication. As the network 140 to which the medical image processing apparatus 14 is connected via the network controller 126, a known network such as a local area network (LAN) may be used.

Power Supply Device

As the power supply device 128, a large-capacity power supply device such as an uninterruptible power supply (UPS) is used. The power supply device 128 supplies power to each unit of the medical image processing apparatus 14 when the commercial power supply is cut off due to a power failure or the like.

Display Controller

The display controller 130 functions as a display driver that controls the monitor device 16 in accordance with a command signal transmitted from the control unit 120.

Input/Output Interface

The input/output interface 132 communicably connects the medical image processing apparatus 14 and an external device to each other. A communication standard such as Universal Serial Bus (USB) may be used for the input/output interface 132.

Input Controller

The input controller 134 converts the format of a signal input using the input device 15 into a format suitable for processing performed by the medical image processing apparatus 14. Information input from the input device 15 via the input controller 134 is transmitted to each unit via the control unit 120.

Note that the hardware configuration of the medical image processing apparatus 14 illustrated in FIG. 2 is merely an example. Thus, addition, deletion, and modification may be appropriately made. The hardware configuration of the medical image processing apparatus 14 illustrated in FIG. 2 is applicable to each of embodiments and modifications described below.

Medical Image Processing Apparatus According to First Embodiment

Description of Functional Blocks

FIG. 3 is a functional block diagram of the medical image processing apparatus according to a first embodiment. The medical image processing apparatus 14 includes an image acquisition unit 40, a region-of-interest detection unit 41, an emphasis region setting unit 42, an update interval setting unit 43, a display control unit 44, and a storage unit 46.

The image acquisition unit 40 acquires the endoscopic image 38 from the processor device 12. The image acquisition unit 40 stores the endoscopic image 38 in an endoscopic image storage unit 47.

The image acquisition unit 40 may acquire the endoscopic image 38 from the processor device 12 via an information storage medium such as a memory card. The image acquisition unit 40 may acquire the endoscopic image 38 via the network 140 illustrated in FIG. 2.

The image acquisition unit 40 may acquire a moving image 38a constituted by time-series frame images 38b. The image acquisition unit 40 may acquire the still image 39 in the case where still image capturing is performed during capturing of the moving image 38a.

The region-of-interest detection unit 41 detects a region of interest from the endoscopic image 38. The region-of-interest detection unit 41 may divide the frame image 38b constituting the endoscopic image 38 into a plurality of local regions, calculate feature quantities for the respective local regions, and detect a region of interest on the basis of the feature quantities for the respective local regions.

The emphasis region setting unit 42 sets an emphasis region for emphasizing the region of interest detected from the endoscopic image 38. The emphasis region setting unit 42 may set a frame enclosing the region of interest as an emphasis region. The emphasis region setting unit 42 may set emphasis regions for all the endoscopic images 38 in which the region of interest is detected.

The emphasis region setting unit 42 may set an emphasis region on the basis of region-of-interest coordinate values that represent the location of the region of interest. A two-dimensional orthogonal coordinate system may be used as a coordinate system used for representing the location of the region of interest and the location of the emphasis region.

The emphasis region setting unit 42 may acquire, as the coordinate values of the region of interest, coordinate values of the center of gravity of the region of interest. The emphasis region setting unit 42 may acquire, as the coordinate values of the region of interest, coordinate values on a closed curve constituting an edge of the region of interest. The emphasis region setting unit 42 may set, as the emphasis region, a quadrangle in which the closed curve constituting the edge of the region of interest inscribes. Instead of a quadrangle, a circle or a polygonal shape other than a quadrangle may be used as the emphasis region.

The update interval setting unit 43 sets an update interval of the emphasis region when the emphasis region is displayed to be superimposed on the endoscopic image 38 using the monitor device 16. The update interval setting unit 43 sets, as the update interval of the emphasis region, an update interval exceeding an update interval used for the endoscopic image 38. The update interval means an interval between any update timing and a next update timing. The update interval may be read as an update period.

The update interval setting unit 43 may acquire information, indicating the update interval, input using the input device 15. That is, the medical image processing apparatus 14 may include a signal reception unit that receives a signal indicating the update interval. An input/output interface for connecting the input device 15 may be used as the signal reception unit.

The display control unit 44 transmits, to the monitor device 16, a display control signal for displaying the endoscopic image 38 and the emphasis region on the monitor device 16. The display control unit 44 updates the endoscopic image 38 using a predetermined update interval. The display control unit 44 updates the emphasis region using the update interval of the emphasis region set using the update interval setting unit 43.

The monitor device 16 acquires the display control signal transmitted from the display control unit 44 and displays the endoscopic image 38 and the emphasis region. The monitor device 16 may display the emphasis region to be superimposed on the endoscopic image 38.

The storage unit 46 includes the endoscopic image storage unit 47, a region-of-interest storage unit 48, and an emphasis region storage unit 49. The endoscopic image storage unit 47 stores the endoscopic image 38 acquired using the image acquisition unit 40.

The region-of-interest storage unit 48 stores information on the region of interest. The region-of-interest storage unit 48 may store information on the region of interest associated with the endoscopic image 38 in which the region of interest is detected. As the information on the region of interest, coordinate values of the region of interest in the endoscopic image 38 may be used. The coordinate values of the region of interest are the same as the coordinate values of the region of interest used when the emphasis region is set.

The emphasis region storage unit 49 stores information on the emphasis region. The emphasis region storage unit 49 may store information on the emphasis region associated with the endoscopic image 38 in which the emphasis region is set.

As the storage unit 46, one or more storage elements may be used. That is, the storage unit 46 may include three storage elements respectively corresponding to the endoscopic image storage unit 47, the region-of-interest storage unit 48, and the emphasis region storage unit 49. For each of the endoscopic image storage unit 47, the region-of-interest storage unit 48, and the emphasis region storage unit 49, a plurality of storage elements may be used. Further, two or all of the endoscopic image storage unit 47, the region-of-interest storage unit 48, and the emphasis region storage unit 49 may be constituted by a single storage element.

Update Interval of Endoscopic Image and Update Interval of Emphasis Region

The medical image processing apparatus 14 according to the present embodiment detects a region of interest from the endoscopic image 38, sets an emphasis region for emphasizing the region of interest, and assists in making a diagnosis on the basis of the region of interest and the emphasis region. On the other hand, when the emphasis region for emphasizing the region of interest changes in each frame, flickering may occur on the screen and may hinder a doctor from making a diagnosis.

Accordingly, the medical image processing apparatus 14 according to the present embodiment performs updating using different intervals for a process of displaying the emphasis region and a process of displaying the endoscopic image 38. Consequently, flickering on the screen caused by the change in the emphasis region may be suppressed.

Figure 4:
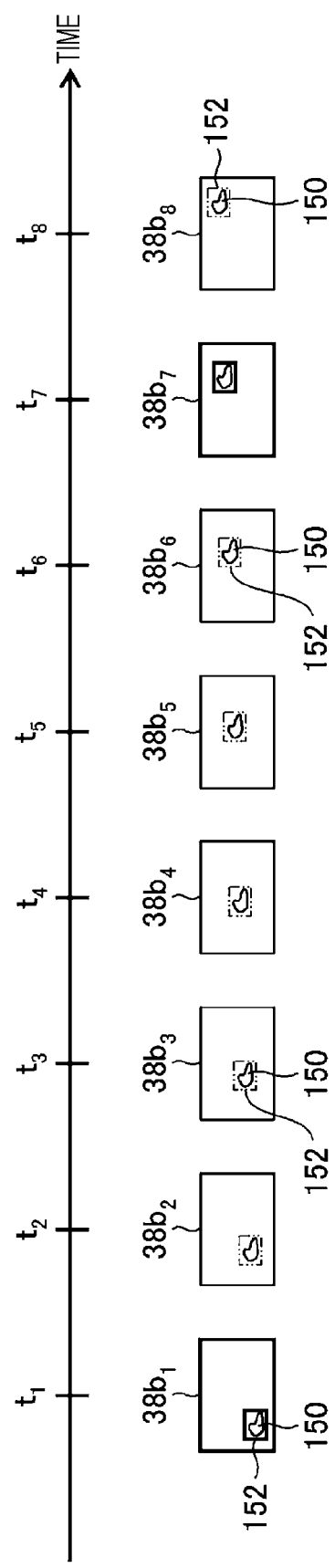
FIG. 4 is an explanatory diagram of update intervals of an endoscopic image and an emphasis region.

FIG. 4 is an explanatory diagram of update intervals of an endoscopic image and an emphasis region. FIG. 4 illustrates a concept of delaying updating of the emphasis region. A timing $t_1$ to a timing $t_8$ illustrated in FIG. 4 represent timings at which display of the endoscopic image 38 is updated. FIG. 4 illustrates eight frame images 38b from a frame image $38b_1$ to a frame images $38b_8$ at timings from the timing $t_1$ to the timing $t_8$ at which display of the endoscopic image 38 is updated.

The region of interest is detected in each frame image 38b. That is, a region of interest 150 is detected in the frame images $38b_1$ to $38b_8$. FIG. 4 schematically illustrates the region of interest 150. In FIG. 4, illustration of reference sign 150 representing the region of interest is appropriately omitted. The same applies to an emphasis region 152 described later.

As the update rate of the frame images 38b, for example, a setting value set in advance in the system, such as 30 frames per second, may be used. When the update rate is equal to 30 frames per second, the update interval is equal to 0.03 seconds.

The emphasis region 152 corresponding to the region of interest 150 is set on each of the frame images $38b_1$ to $38b_8$. On the other hand, display of the emphasis region 152 is updated at the timing $t_1$ and timing $t_7$. However, display of the emphasis region 152 is not updated at the timings $t_2$ to $t_6$ and at the timing $t_8$.

FIG. 4 illustrates an example in which the update rate of the emphasis region 152 is set to be one sixth of the update rate of the frame images 38b. When the update rate of the frame images 38b is equal to 30 frames per second, the update rate of the emphasis region 152 is 5 frames per second. When n denotes any number greater than 1, the update rate of the emphasis region 152 may be set to be 1/n of the update rate of the frame images 38b. n may be an integer of 2 or greater.

As described above, even when the location of the region of interest 150 changes in each frame image 38b, the update interval of the display of the emphasis region 152 is longer than the update interval of the display of the frame image 38b. Thus, when the emphasis region 152 for emphasizing the region of interest 150 is displayed, the location of the emphasis region 152 is updated with a delay with respect to the update of the frame image 38b. Consequently, flickering of the endoscopic image 38 may be suppressed.

In the present embodiment, the update rate represented using the number of frames per second is described as an example of the setting of the update interval of the display of the emphasis region 152. Alternatively, a period representing the update interval of the display of the emphasis region 152 may be set. When m denotes any number greater than 1, the update interval of the emphasis region 152 may be set to be m times the update interval of the frame images 38b. m may be an integer of 2 or greater.

The update interval of the display of the emphasis region 152 may be set in accordance with the update rate of the frame images 38b. As described above, the update rate of the display of the emphasis region 152 may be set to one sixth of the update rate of the frame images 38b.

Specific Example of Updating of Display of Emphasis Region

Figure 5:
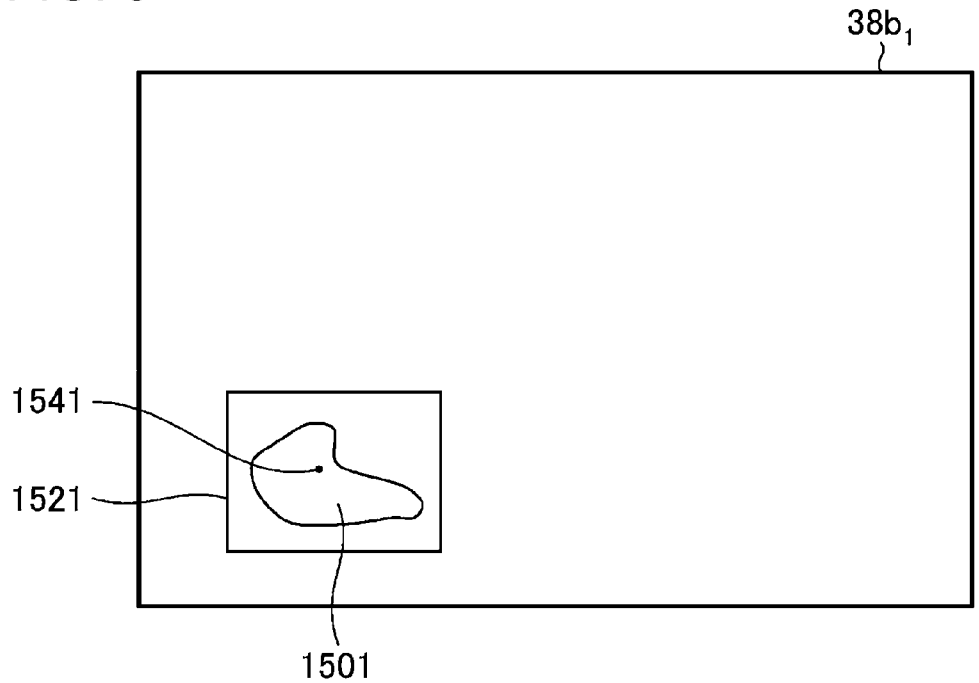
FIG. 5 is a schematic diagram of a frame image at a timing $t_1$ in FIG. 4.

FIG. 5 is a schematic diagram of a frame image at the timing $t_1$ in FIG. 4. In the frame image $38b_1$ illustrated in FIG. 5, a region of interest 1501 is detected, an emphasis region 1521 based on the region of interest 1501 is set, and the emphasis region 1521 is displayed to be superimposed on the region of interest 1501.

The emphasis region 1521 is set on the basis of coordinate values of a center of gravity 1541 of the region of interest 1501. When the region of interest 1501 is detected, the coordinate values of the center of gravity 1541 of the region of interest 1501 are calculated. The coordinate values of the center of gravity 1541 of the region of interest 1501 are set as coordinate values of the center of gravity of the emphasis region 1521.

Coordinate values of a closed curve constituting the edge of the region of interest 1501 are calculated. On the basis of the coordinate values of the closed curve constituting the edge of the region of interest 1501, coordinate values of individual sides of a quadrangle which is the emphasis region 1521 are calculated.

Figure 6:
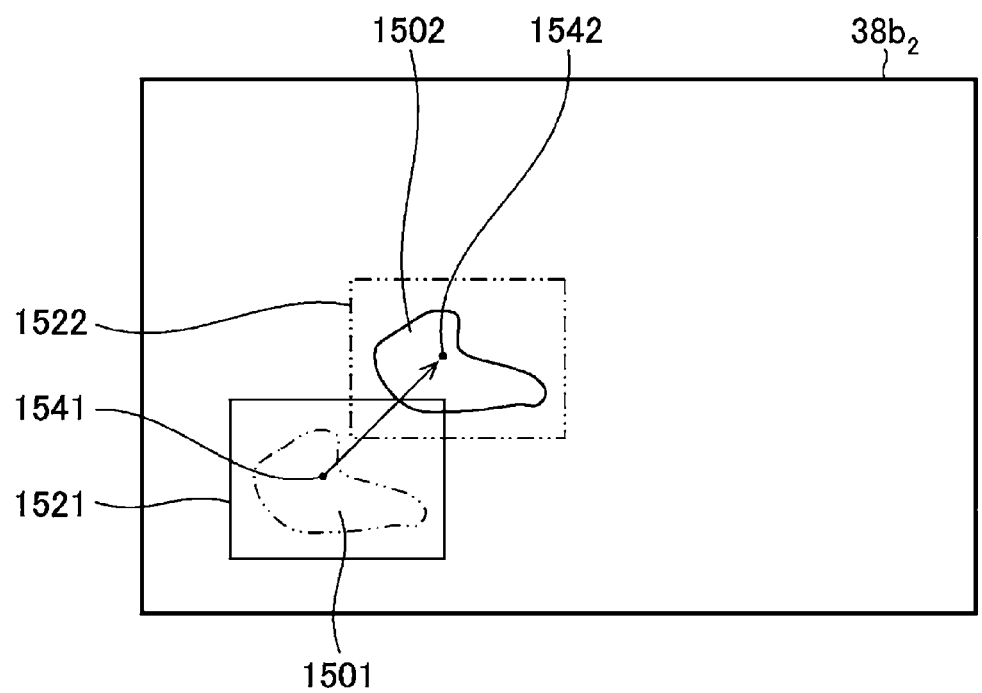
FIG. 6 is a schematic diagram of a frame image at a timing $t_2$ in FIG. 4.

FIG. 6 is a schematic diagram of a frame image at the timing $t_2$ in FIG. 4. In the frame image $38b_2$ illustrated in FIG. 6, a region of interest 1502 is detected. In the frame image $38b_2$, an emphasis region 1522 is set. However, the display is not updated to the emphasis region 1522. That is, in the frame image $38b_2$, the emphasis region 1521 updated in the immediately preceding frame image $38b_1$ is displayed instead of the emphasis region 1522 based on the region of interest 1502 detected from the frame image $38b_2$.

Note that reference sign 1542 denotes the center of gravity of the region of interest 1502 in the frame image $38b2$. An arrow line starting from the center of gravity 1541 and ending at the center of gravity 1542 indicates that the location has moved to the location of the region of interest 1502 in the frame image $38b_2$ from the location of the region of interest 1501 in the frame image $38b_1$.

Figure 7:
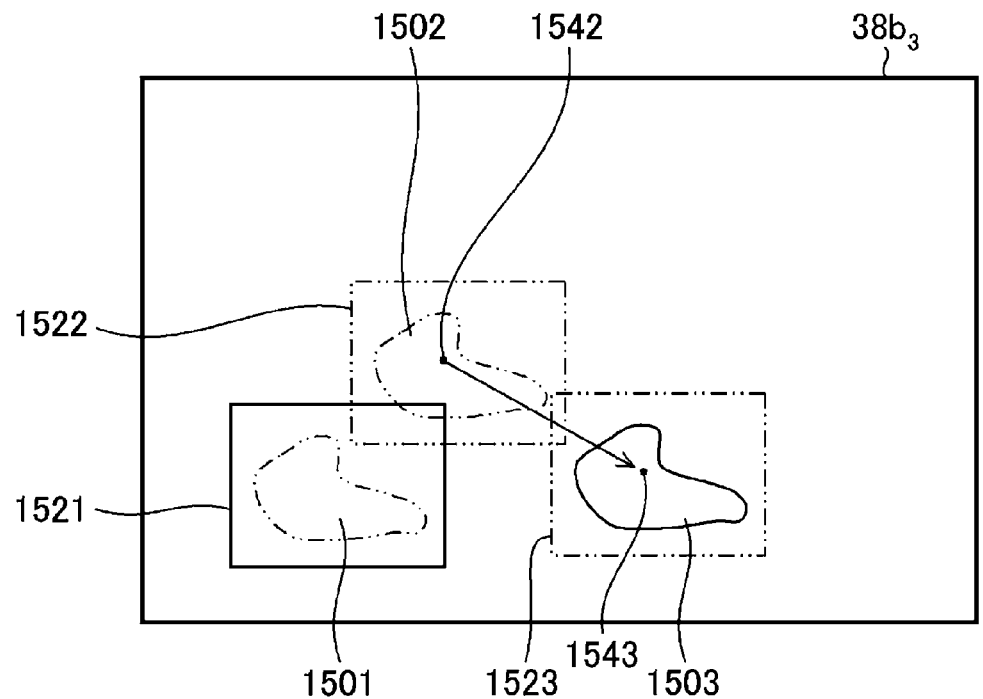
FIG. 7 is a schematic diagram of a frame image at a timing $t_3$ in FIG. 4.

FIG. 7 is a schematic diagram of a frame image at the timing $t_3$ in FIG. 4. Also in the frame image $38b_3$, an emphasis region 1523 based on a region of interest 1503 is set but the display is not updated to the emphasis region 1523. That is, when the region of interest 1503 is detected in the frame image $38b_3$ and the emphasis region 1523 is set, the display is updated to the region of interest 1503 in the frame image $38b_3$. However, the emphasis region 1521 set in the frame image $38b_1$ that precedes by two frames is displayed in the frame image $38b_3$.

Note that reference sign 1543 denotes the center of gravity of the region of interest 1503 in the frame image $38b_3$. An arrow line starting from the center of gravity 1542 and ending at the center of gravity 1543 indicates that the location has moved to the location of the region of interest 1503 in the frame image $38b_3$ from the location of the region of interest 1502 in the frame image $38b_2$. Detailed illustration of the frame image $38b_4$ at the timing $t_4$, the frame image $38b_5$ at the timing $t_5$, and the frame image $38b_6$ the timing $t_6$ in FIG. 4 is omitted.

Figure 8:
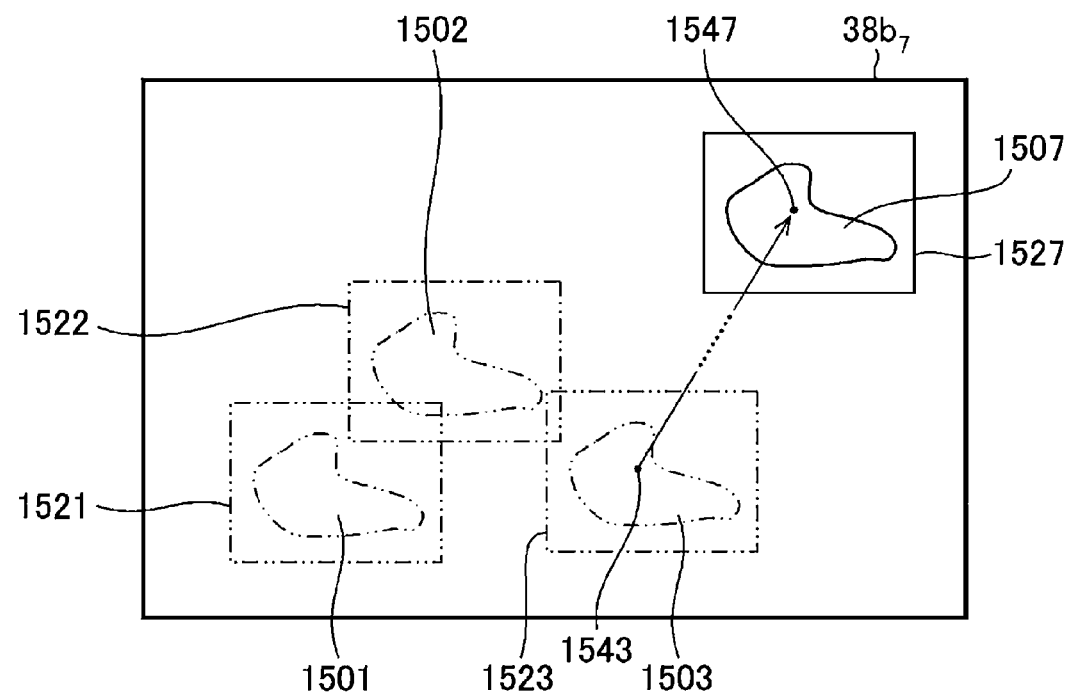
FIG. 8 is a schematic diagram of a frame image at a timing $t_7$ in FIG. 4.

FIG. 8 is a schematic diagram of a frame image at the timing $t_7$ in FIG. 4. When a region of interest 1507 is detected from the frame image $38b_7$, an emphasis region 1527 based on the region of interest 1507 is set. In the frame image $38b_7$, display is updated to the region of interest 1507 and to the emphasis region 1527.

Note that reference sign 1547 denotes the center of gravity of the region of interest 1507 in the frame image $38b_7$. An arrow line starting from the center of gravity 1543 and ending at the center of gravity 1547 indicates that the location has moved to the location of the region of interest 1507 in the frame image $38b_7$ from the location of the region of interest 1503 in the frame image $38b_4$ through the locations of the region of interest 150 in the frame images not illustrated. Detailed illustration of the frame image $38b_8$ at the timing $t_8$ in FIG. 4 is omitted.

Flowchart of Medical Image Processing Method

Figure 9:
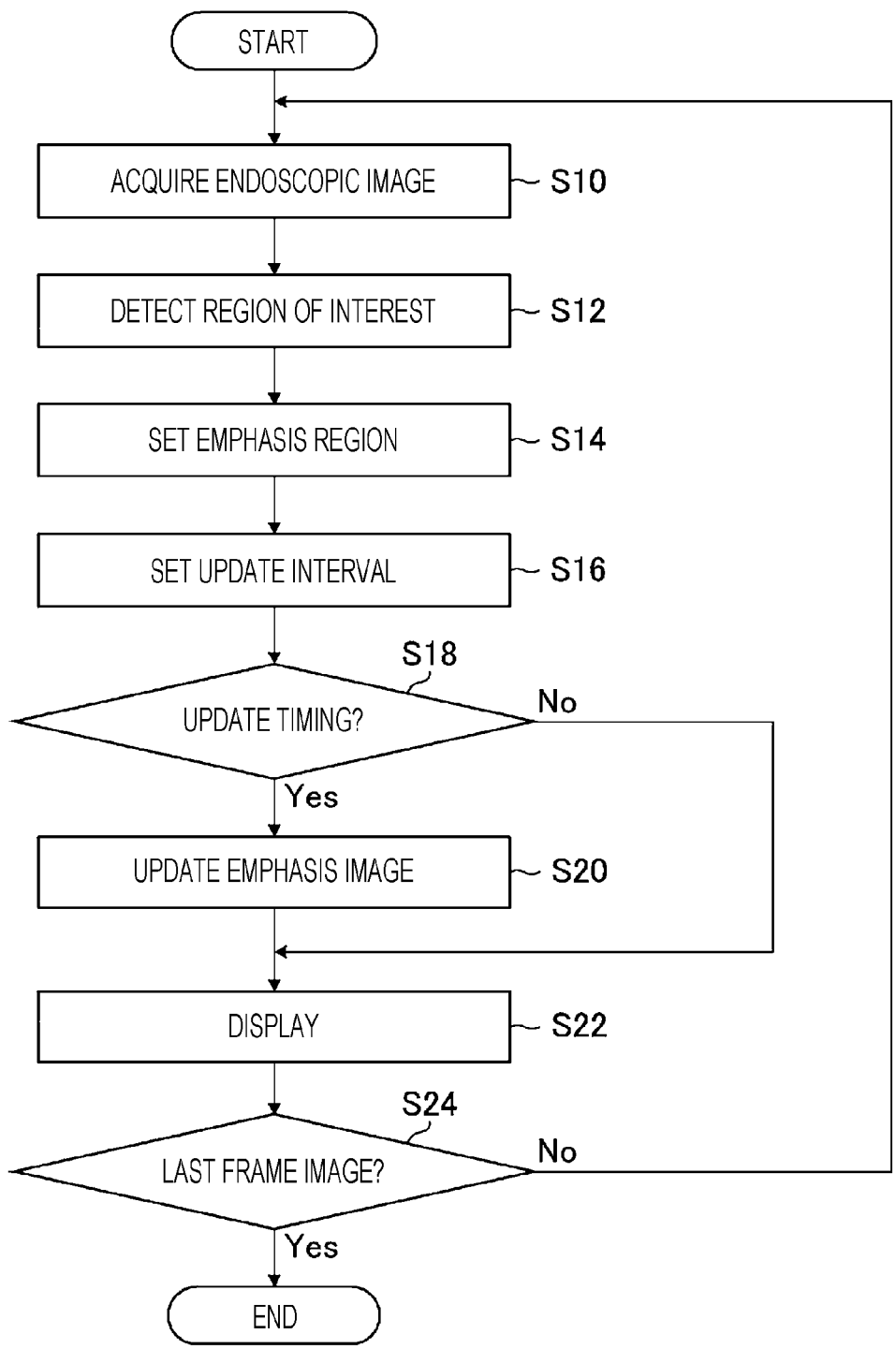
FIG. 9 is a flowchart of a medical image processing method according to the first embodiment.

FIG. 9 is a flowchart of a medical image processing method according to the first embodiment. The medical image processing method according to the first embodiment includes an endoscopic image acquisition step S10, a region-of-interest detection step S12, an emphasis region setting step S14, an update interval setting step S16, an update timing determination step S18, an emphasis region update step S20, a display step S22, and a last frame image determination step S24.

In the endoscopic image acquisition step S10, the medical image processing apparatus 14 illustrated in FIG. 3 acquires, using the image acquisition unit 40, the frame image 38b constituting the endoscopic image 38 from the endoscope system 9. After the endoscopic image acquisition step S10, the process proceeds to the region-of-interest detection step S12.

In the region-of-interest detection step S12, the region-of-interest detection unit 41 detects the region of interest 150 from the frame image 38b and identifies the location and shape of the region of interest 150. The medical image processing apparatus 14 stores, as information on the region of interest 150, information on coordinate values representing the location of the region of interest 150 and information on the shape of the region of interest 150 in the region-of-interest storage unit 48. After the region-of-interest detection step S12, the process proceeds to the emphasis region setting step S14.

In the emphasis region setting step S14, the emphasis region setting unit 42 sets the location and shape of the emphasis region 152 on the basis of the location and shape of the region of interest 150 detected in the region-of-interest detection step S12. The emphasis region setting unit 42 stores, as information on the emphasis region 152, information on the location of the emphasis region 152 and information on the shape of the emphasis region 152 in the emphasis region storage unit 49. After the emphasis region setting step S14, the process proceeds to the update interval setting step S16.

In the update interval setting step S16, the update interval setting unit 43 sets, as the update interval of the emphasis region 152, an update interval exceeding the update interval of the frame images 38b that is set in advance. The update interval setting unit 43 may store information on the update interval in the storage unit 46.

The update interval setting step S16 may be performed as a preceding step of the emphasis region setting step S14 such as before the endoscopic image acquisition step S10. That is, the update interval setting step S16 may be performed before an endoscopic examination is started or during an endoscopic examination. In the update interval setting step S16, a predetermined initial value of the update interval of the display of the emphasis region 152 may be changed.

In the update interval setting step S16, a value input as the update interval of the display of the emphasis region 152 by a user using the input device 15 may be acquired. After the update interval setting step S16, the process proceeds to the update timing determination step S18.

In the update timing determination step S18, the display control unit 44 determines whether it is the update timing of the emphasis region 152. In the update timing determination step S18, if the display control unit 44 determines that it is not the predetermined update timing, No is obtained. Thus, the process proceeds to the display step S22 without updating the display of the emphasis region 152. On the other hand, if the display control unit 44 determines that it is the predetermined update timing, Yes is obtained. Thus, the process proceeds to the emphasis region update step S20.

In the emphasis region update step S20, the display control unit 44 updates the display of the emphasis region 152. After the emphasis region update step S20, the process proceeds to the display step S22. The emphasis region update step S20 described in the embodiment is an example of a display control step of updating display of an emphasis region using an update interval exceeding an update interval of display of a medical image.

In the display step S22, the display control unit 44 transmits a signal representing the region of interest 150 and the emphasis region 152 to the monitor device 16. The monitor device 16 displays the region of interest 150 and the emphasis region 152 on the basis of the signal transmitted from the display control unit 44. After the display step S22, the process proceeds to the last frame image determination step S24.

In the last frame image determination step S24, the image acquisition unit 40 determines whether the frame image 38b acquired in the endoscopic image acquisition step S10 is the last frame image 38b. If a period over which the next frame image 38b is not input since acquisition of the frame image 38b is longer than or equal to a predetermined period, the image acquisition unit 40 may determine that the last frame image 38b has been acquired. The image acquisition unit 40 may determine that the last frame image 38b has been acquired, in response to receipt of a signal indicating the end of transmission of the endoscopic image 38.

In the last frame image determination step S24, if the image acquisition unit 40 determines that the frame image 38b that is not the last frame image 38b is acquired, No is obtained. Thus, the process proceeds to the endoscopic image acquisition step S10. Thereafter, the individual steps from the endoscopic image acquisition step S24 to the last frame image determination step S10 are repeatedly performed until Yes is obtained in the last frame image determination step S24.

On the other hand, in the last frame image determination step S24, if the image acquisition unit 40 determines that the last frame image 38b is acquired, No is obtained. After the predetermined termination processing is performed, the medical image processing method ends.

Modifications of Emphasis Region Setting
First Modification

In emphasis region setting according to a first modification, the emphasis region 152 in a frame of interest is set using the emphasis regions 152 set in the frame images 38b from an immediately preceding update frame to the frame of interest. The immediately preceding update frame is the frame image 38b in which the display of the emphasis region 152 is updated last time. The frame of interest is the frame image 38b in which the display of the emphasis region 152 is to be updated.

Figure 10:
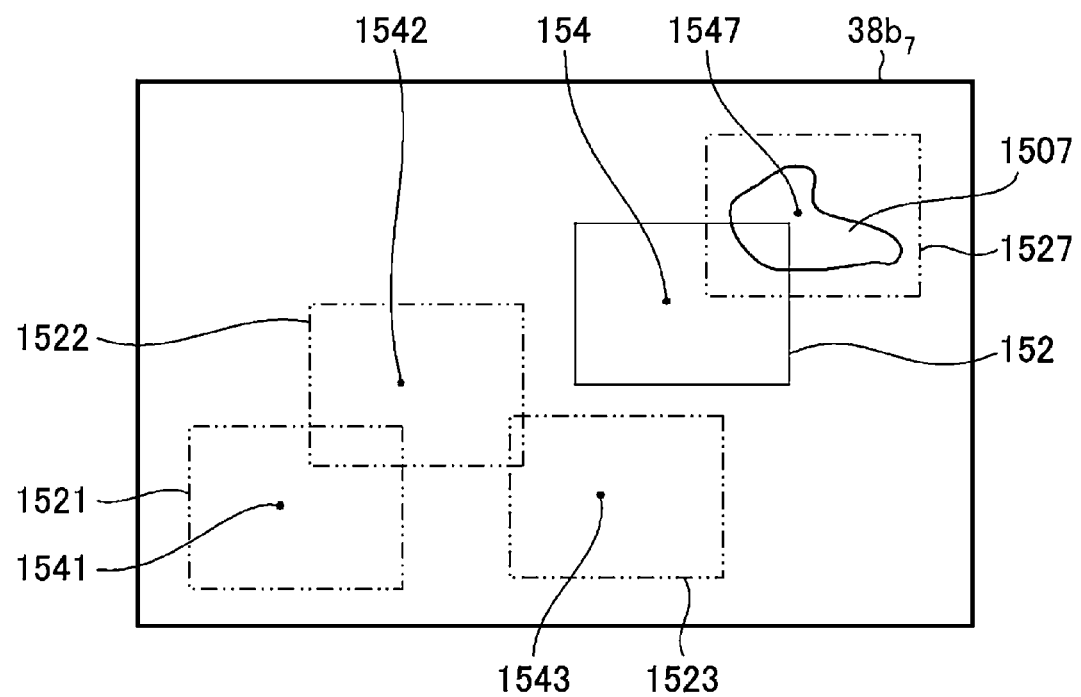
FIG. 10 is an explanatory diagram of a first modification of emphasis region setting.

FIG. 10 is an explanatory diagram of the first modification of emphasis region setting. The frame image $38b_7$ illustrated in FIG. 10 is the frame image 38b at the timing $t_7$ illustrated in FIG. 4. As the location of the emphasis region 152 displayed in the frame image $38b_7$, an average location from the emphasis region 1521 of the frame image $38b_1$, which is the frame image 38b before the frame image $38b_7$, to the emphasis region 1527 of the frame image $38b_7$ is used. Instead of the average location, the location of the emphasis region of any frame image from the emphasis region 1521 of the frame image $38b_1$ to the emphasis region 1527 of the frame image $38b_7$ may be used as the location of the emphasis region 152 displayed in the frame image $38b_7$.

If the display of the emphasis region 1521 is maintained from the timing $t_1$ to the timing $t_6$ in FIG. 4 and then the emphasis region 1527 is displayed at the timing $t_7$, flickering may occur.

Accordingly, coordinate values of a center of gravity 154 is calculated, as the location of the emphasis region at the timing $t_7$, using coordinate values from the coordinate values of the center of gravity 1541 to the coordinate values of the center of gravity 1547. The location of the center of gravity 154 is set as the location of the emphasis region 152.

For example, as the coordinate values of the center of gravity 154, an average value of the coordinate values from the coordinate values of the center of gravity 1541 to the coordinate values of the center of gravity 1547 may be used. All the coordinate values from the coordinate values of the center of gravity 1541 to the coordinate values of the center of gravity 1547 need not be used, and any two or more coordinate values from the coordinate values of the center of gravity 1541 to the coordinate values of the center of gravity 1547 may be used as the coordinate values of the center of gravity 154.

Second Modification

Figure 11:
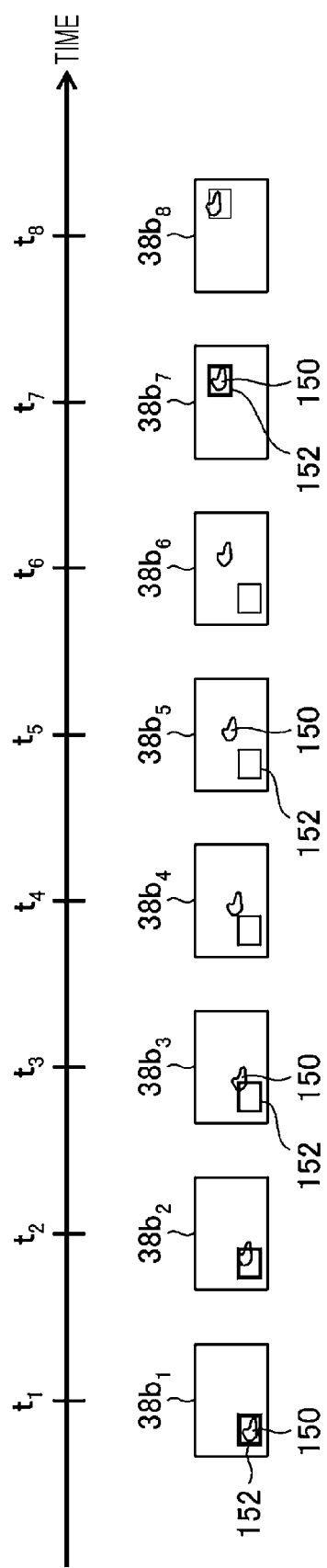
FIG. 11 is an explanatory diagram of a second modification of the emphasis region setting.

FIG. 11 is an explanatory diagram of a second modification of the emphasis region setting. In the emphasis region setting according to the second modification, the display of the emphasis region 152 is weakened as time passes in the frame images 38b at timings other than the update timings of the display of the emphasis region 152. Among the frame images 38b illustrated in FIG. 11, the frame images 38b at timings other than the update timings are the frame image $38b_2$, the frame images $38b_3$, the frame image $38b_4$, the frame image $38b_5$, the frame image $38b_6$, and the frame image $38b_8$.

An example of weakening the display of the emphasis region 152 may be an example in which the density of the frame indicating the emphasis region 152 is decreased. The color may be changed when the density is decreased. Other examples of weakening the display of the emphasis region 152 include an example of reducing the thickness of the frame indicating the emphasis region 152 and an example of changing the type of the line of the frame indicating the emphasis region 152. The frame indicating the emphasis region 152 may be changed continuously or may be changed in steps.

Other examples of weakening the display of the emphasis region 152 include an example of causing the frame indicating the emphasis region 152 to blink. The frame indicating the emphasis region 152 may be caused to blink at a certain cycle, or the cycle of blinking may be changed over time.

Weakening the display of the emphasis region 152 in this way may reduce the visual strangeness caused by the change in the location of the emphasis region 152 and may suppress flickering.

Third Modification

Figure 12:
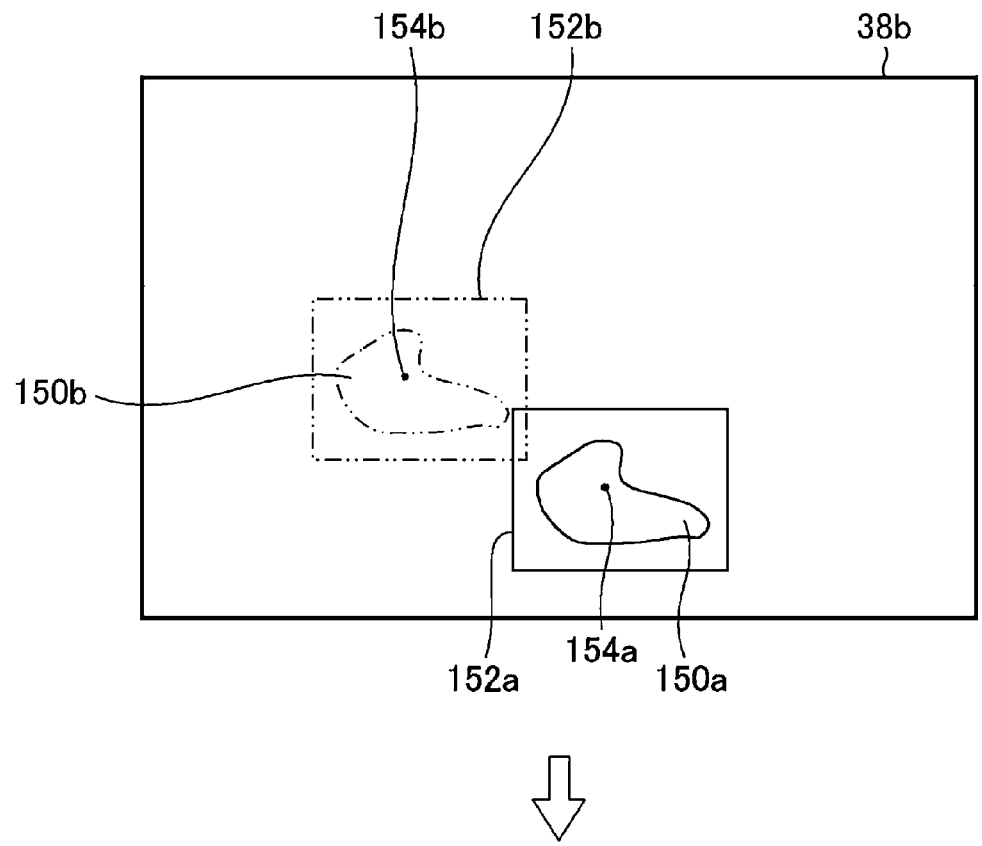
FIG. 12 is an explanatory diagram of a third modification of the emphasis region setting.
Figure 12:
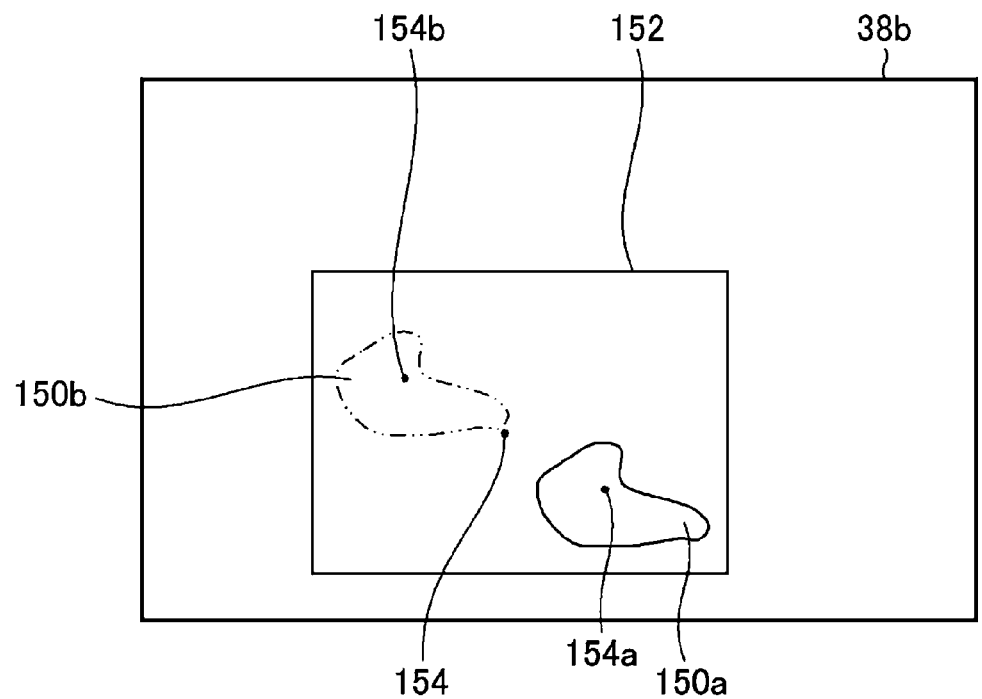

FIG. 12 is an explanatory diagram of a third modification of the emphasis region setting. In image processing according to the third modification, the emphasis regions 152 set in the plurality of frame images 38b are merged. FIG. 12 illustrates an example in which an emphasis region 152b in the immediately preceding frame image 38b is merged with an emphasis region 152a in the current frame image 38b. The immediately preceding frame image 38b of the current frame image 38b described in the embodiment is an example of a past frame.

In the frame image 38b illustrated in the upper part of FIG. 12, a region of interest 150a is detected and the emphasis region 152a based on the region of interest 150a is set. Reference sign 154a in the frame image 38b illustrated in the upper part of FIG. 12 denotes the center of gravity of the region of interest 150a.

In the frame image 38b illustrated in the upper part of FIG. 12, a region of interest 150b detected in the immediately preceding frame image 38b, the emphasis region 152b set on the basis of the region of interest 150b, and a center of gravity 154b of the region of interest 150b are illustrated.

In the frame image 38b illustrated in the lower part of FIG. 12, the emphasis region 152 obtained by merging the emphasis region 152a and the emphasis region 152b is displayed. The coordinate values of the center of gravity 154 used in setting the emphasis region 152 are derived using the coordinate values of the center of gravity 154a of the region of interest 150a and the coordinate values of the center of gravity 154b of the region of interest 150b. The coordinate values of the frame representing the emphasis region 152 are derived on the basis of the coordinate values of the center of gravity 154, the coordinate values of the frame representing the emphasis region 152a, and the coordinate values of the frame representing the emphasis region 152b.

Merging the emphasis regions 152 in this manner may suppress flickering caused by the change in the emphasis region 152. In this modification, the example of merging two emphasis regions 152 is described. However, three or more emphasis regions 152 may be merged.

Fourth Modification

In the endoscopic image 38, the region of interest 150 may not be detected although the region of interest 150 is present. The presence of the frame image 38b in which the region of interest 150 is not detected may serve as a cause of flickering. Accordingly, by integrating the region of interest 150 with respect to time, flickering may be suppressed.

Effects of First Embodiment

According to the medical image processing apparatus 14 of the first embodiment configured as described above, the following effects can be obtained.

[1]

A period exceeding an update interval of display of the endoscopic image 38 is used as an update interval of display of the emphasis region 152. Consequently, the emphasis region 152 is updated with a delay with respect to the update of the endoscopic image 38, and a flickering caused in a screen displaying the endoscopic image 38 by a change in the location of the emphasis region 152 may be suppressed.

[2]

In the frame images 38b displayed after the emphasis region 152 is updated, the location of the emphasis region 152 updated last is maintained until the frame image 38b in which the emphasis region 152 is updated next. Consequently, a movement in the location of the emphasis region 152 in the frame images 38b is suppressed, and flickering in the screen displaying the endoscopic image 38 may be suppressed.

[3]

In the frame image 38b in which the emphasis region 152 is updated, the emphasis region 152 is displayed at an average location in two or more frame images 38b preceding the frame image 38b in which the emphasis region 152 is updated. Consequently, a movement in the location of the emphasis region 152 in the frame images 38b is suppressed, and flickering in the screen displaying the endoscopic image 38 may be suppressed.

[4]

In the frame images 38b at timings other than the update timings, the display of the emphasis region 152 is weakened as time passes. Consequently, a change in the emphasis region 152 in the frame images 38b is suppressed, and flickering in the screen displaying the endoscopic image 38 may be suppressed.

Medical Image Processing Apparatus According to Second Embodiment

Figure 13:
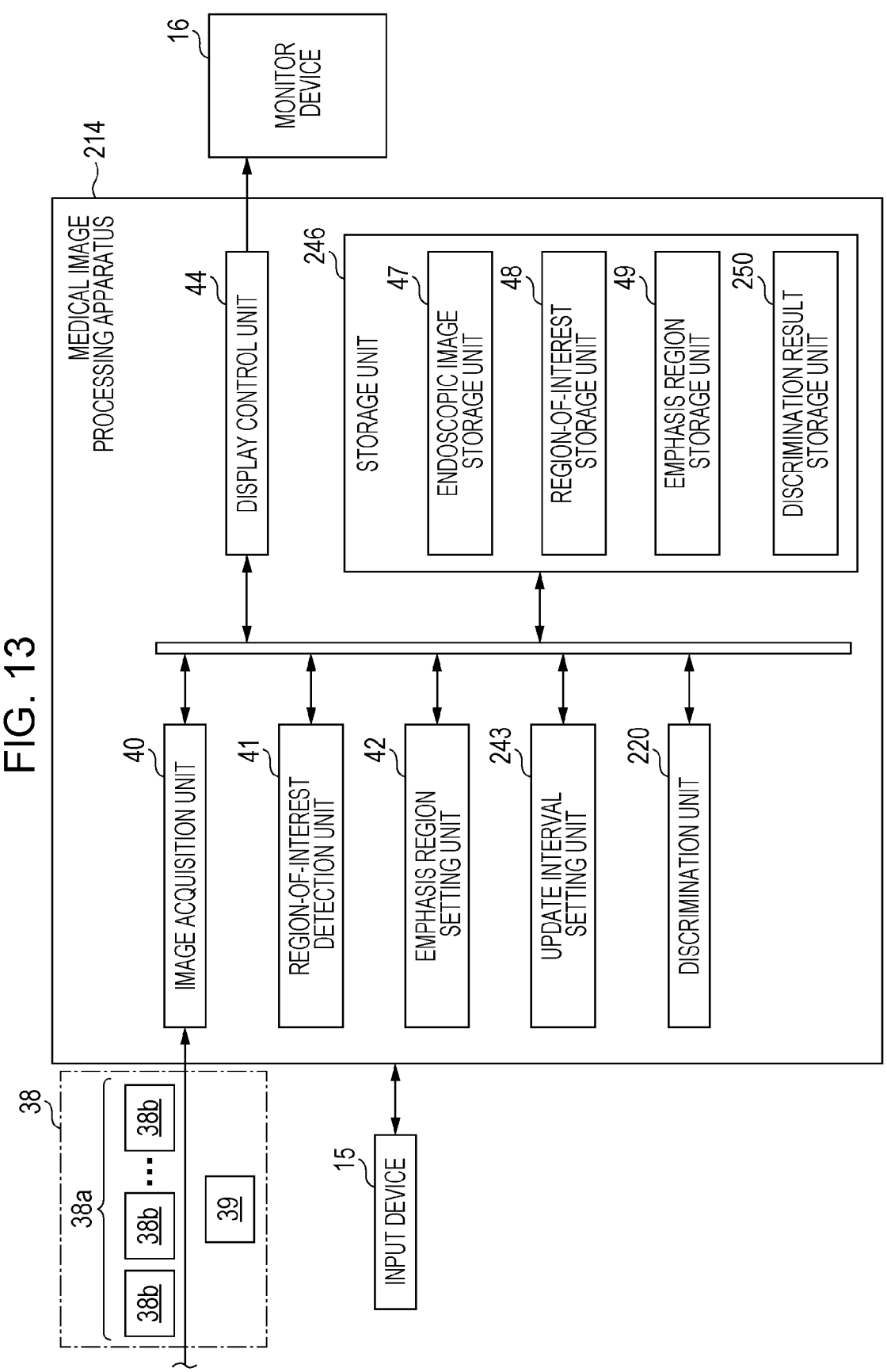
FIG. 13 is a functional block diagram of a medical image processing apparatus according to a second embodiment.

FIG. 13 is a functional block diagram of a medical image processing apparatus according to a second embodiment. A medical image processing apparatus 214 according to the second embodiment includes a discrimination unit 220. A storage unit 246 includes a discrimination result storage unit 250.

The discrimination unit 220 may discriminate whether the region of interest 150 is a lesion. The discrimination unit 220 may discriminate whether the region of interest 150 is a tumor or a non-tumor. The discrimination unit 220 may discriminate whether the region of interest 150 is an inflammation region. The medical image processing apparatus 214 may perform discrimination on the endoscopic image 38 using information on a blood vessel pattern, information on a color in a body cavity when a coloring agent is administered into the body cavity, and the like instead of the detection result obtained by the region-of-interest detection unit 41.

Predetermined classifications such as the NICE classification and the JNET classification may be used in discrimination performed using the discrimination unit 220. Note that NICE is an abbreviation for NBI International Colorectal Endoscopic Classification. JNET is an abbreviation for The Japan NBI Expert Team. NBI is an abbreviation for Narrow Band Imaging.

The display control unit 44 may read out the discrimination result from the discrimination result storage unit 250 and transmit a signal indicating the discrimination result to the monitor device 16. The monitor device 16 may display the discrimination result to be superimposed on the endoscopic image 38. The monitor device 16 may display the endoscopic image 38 and the discrimination result in different regions. As the discrimination result, text information representing the discrimination result may be used.

When updating the display of the discrimination result, the display control unit 44 may use an update interval exceeding an update interval of display of the endoscopic image 38. The display control unit 44 may use the update interval of the display of the emphasis region when updating display of the discrimination result.

An update interval setting unit 243 may set the update interval of the display of the discrimination result. The update interval setting unit 243 may include an emphasis update interval setting unit that sets an update interval of display of an emphasis region, and a discrimination update interval setting unit that sets an update interval of display of a discrimination result.

Modifications

The medical image processing apparatus 214 may set the update interval of the display of the emphasis region 152 in accordance with the discrimination result of the endoscopic image 38. For example, if the discrimination result is inflammation, the inflammation is present in a wide range of the endoscopic image. Thus, the emphasis region 152 for emphasizing the inflammation is wider than the emphasis region 152 of a tumor or the like. Therefore, the update interval of the display of the emphasis region 152 may be set longer in the case where the discrimination result is inflammation than in the case of other discrimination results.

A distance over which the emphasis region 152 of a wide range moves between the frame images 38b is considered to be relatively short. Therefore, the emphasis region 152 need not be updated in a short time. If the update interval of the display of the emphasis region 152 is set long, an influence of such a setting on visual recognition of the endoscopic image 38 is small and flickering of the endoscopic image 38 may be effectively suppressed.

The update interval of the display of the emphasis region 152 may be set to be shorter in the case where the discrimination result is a regional lesion such as cancer than in the case of other discrimination results. Consequently, when the discrimination result is a regional lesion such as cancer, an influence on visual recognition of the endoscopic image 38 is suppressed and flickering of the endoscopic image 38 may be effectively suppressed.

Effects of Second Embodiment

According to the medical image processing apparatus 214 of the second embodiment configured as described above, the following effects can be obtained.

[1]

Automatic discrimination is performed on each frame image 38b of the endoscopic image 38. However, there may be a frame image 38b for which a discrimination result is not obtained, and consequently flickering due to automatic discrimination may occur. Accordingly, when automatic discrimination is performed on the endoscopic images 38 and the discrimination result is displayed, the update interval exceeding the update interval of the display of the endoscopic image 38 is used to update the display of the discrimination result. Consequently, flickering due to the discrimination result may be effectively suppressed.

[2]

As the update interval of the display of the discrimination result, the update interval of the display of the emphasis region 152 is used. Consequently, the display of the discrimination result may be updated using the update interval of the display of the emphasis region.

[3]

In the case where the discrimination result is inflammation, an update interval longer than the update interval of the display of the emphasis region 152, which is used in the case of other discrimination results, is used. Consequently, in the case where the discrimination result is inflammation, flickering of the endoscopic image 38 may be effectively suppressed.

[4]

In the case where the discrimination result is a regional lesion such as cancer, an update interval shorter than the update interval of the display of the emphasis region 152 used in the case of other discrimination results is used. Consequently, when the discrimination result is a regional lesion such as cancer, an influence on visual recognition of the endoscopic image 38 is suppressed and flickering of the endoscopic image 38 may be effectively suppressed.

Medical Image Processing Apparatus According to Third Embodiment

Figure 14:
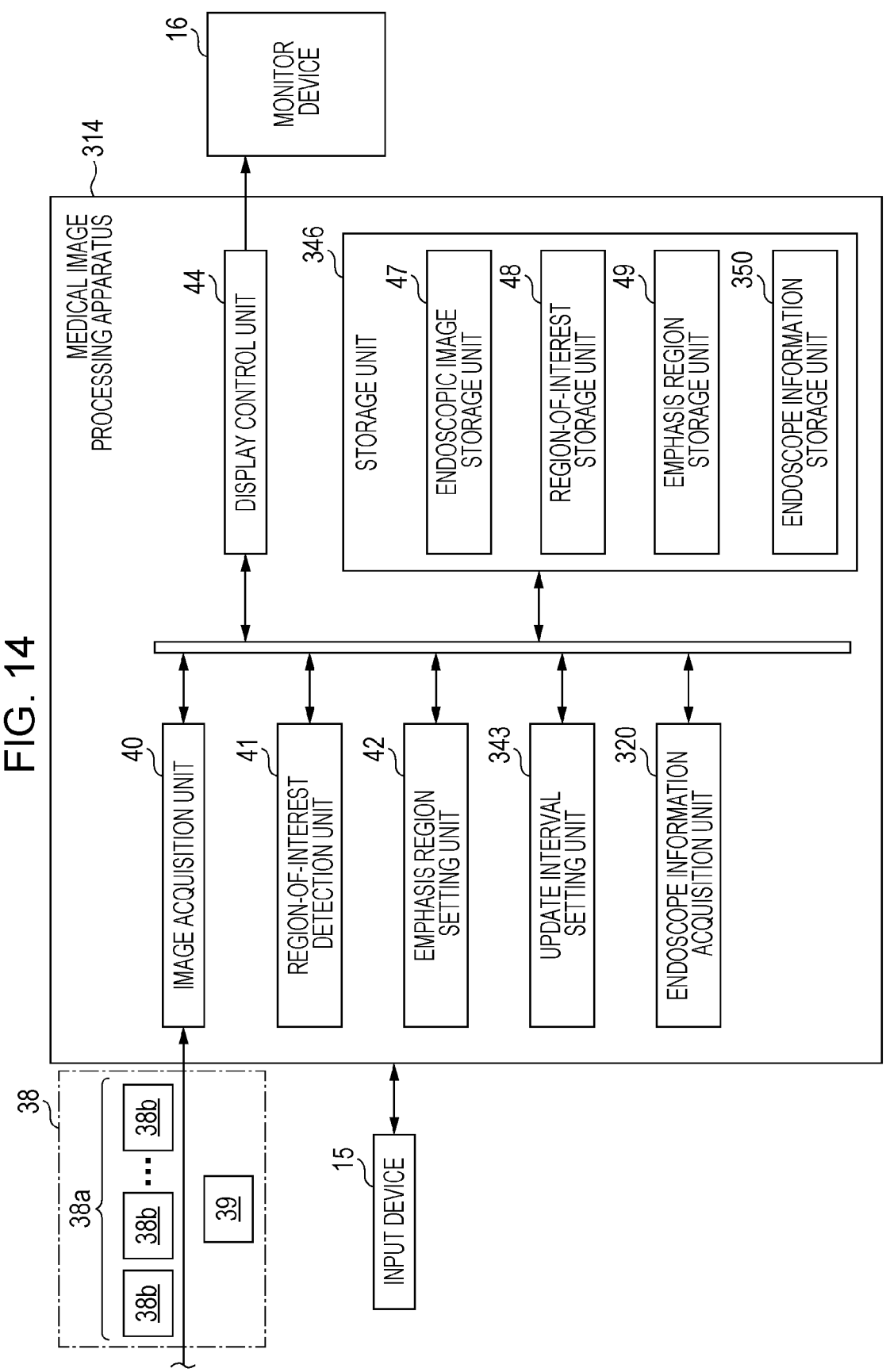
FIG. 14 is a functional block diagram of a medical image processing apparatus according to a third embodiment.

FIG. 14 is a functional block diagram of a medical image processing apparatus according to a third embodiment. A medical image processing apparatus 314 according to the third embodiment includes an endoscope information acquisition unit 320. A storage unit 346 includes an endoscope information storage unit 350.

The endoscope information acquisition unit 320 acquires a moving velocity of the tip part 27 of the endoscope 10. The endoscope information acquisition unit 320 stores the moving velocity of the tip part 27 of the endoscope 10 in the endoscope information storage unit 350.

The moving velocity of the tip part 27 of the endoscope 10 may be derived from a movement vector of the frame images 38b which is derived by performing image analysis processing on the endoscopic image 38. As the moving velocity of the tip part 27 of the endoscope 10, a detection result obtained by a velocity sensor included in the endoscope 10 may be used.

An update interval setting unit 343 sets an update interval of display of the emphasis region 152 in accordance with the moving velocity of the tip part 27 of the endoscope 10. For example, when the moving velocity of the tip part 27 of the endoscope 10 is relatively high, the update interval of the display of the emphasis region 152 is set to be relatively short. When the moving velocity of the tip part 27 of the endoscope 10 is relatively low, the update interval of the display of the emphasis region 152 is set to be relatively long. The moving velocity of the tip part 27 of the endoscope 10 described in the embodiment is an example of a movement of an imaging device.

Note that the term "velocity" used herein may include a concept of a speed which is expressed as an absolute value of the velocity. Herein, velocity and speed can be read interchangeably.

Effects of Third Embodiment

According to the medical image processing apparatus 314 of the third embodiment configured as described above, the following effects can be obtained.

[1]

The update interval of the display of the emphasis region 152 is set in accordance with the moving velocity of the tip part 27 of the endoscope 10. Consequently, even when the moving velocity of the tip part 27 of the endoscope 10 changes, flickering caused by the display of the emphasis region 152 may be suppressed.

[2]

When the moving velocity of the tip part 27 of the endoscope 10 is relatively high, the update interval of the display of the emphasis region 152 is set to a relatively short period. Consequently, even when the change between the frame images 38b is large, the display of the emphasis region 152 may be cause to follow the change.

Modifications of Endoscope System

Modification of Processor Device

The processor device 12 may have the functions of the medical image processing apparatus 14. That is, the processor device 12 and the medical image processing apparatus 14 may be integrated together. In such an embodiment, the display device 13 may also serve as the monitor device 16. The processor device 12 may include a connection terminal to which the input device 15 is connected.

Modification of Illumination Light

One example of the medical image acquirable using the endoscope system 9 according to the present embodiments is a normal-light image acquired by radiating light in a white range or light in a plurality of wavelength ranges as the light in the white range.

Another example of the medical image acquirable using the endoscope system 9 according to the present embodiments is an image acquired by radiating light in a specific wavelength range. A range narrower than the white range may be used as the specific wavelength range. The following modifications may be employed.

First Modification

A first example of the specific wavelength range is a blue range or a green range in a visible range. The wavelength range of the first example includes a wavelength range of 390 nm or more and 450 nm or less or a wavelength range of 530 nm or more and 550 nm or less, and the light of the first example has a peak wavelength in the wavelength range of 390 nm or more and 450 nm or less or the wavelength range of 530 nm or more and 550 nm or less.

Second Modification

A second example of the specific wavelength range is a red range in the visible range. The wavelength range of the second example includes a wavelength range of 585 nm or more and 615 nm or less or a wavelength range of 610 nm or more and 730 nm or less, and the light of the second example has a peak wavelength in the wavelength range of 585 nm or more and 615 nm or less or the wavelength range of 610 nm or more and 730 nm or less.

Third Modification

A third example of the specific wavelength range includes a wavelength range in which an absorption coefficient is different between oxyhemoglobin and deoxyhemoglobin, and the light of the third example has a peak wavelength in the wavelength range in which the absorption coefficient is different between oxyhemoglobin and deoxyhemoglobin. The wavelength range of this third example includes a wavelength range of 400±10 nm, a wavelength range of 440±10 nm, a wavelength range of 470±10 nm, or a wavelength range of 600 nm or more and 750 nm or less, and the light of the third example has a peak wavelength in the wavelength range of 400±10 nm, the wavelength range of 440±10 nm, the wavelength range of 470±10 nm, or the wavelength range of 600 nm or more and 750 nm or less.

Fourth Modification

A fourth example of the specific wavelength range is a wavelength range of excitation light that is used to observe fluorescence emitted by a fluorescent substance in a living body and excites this fluorescent substance. For example, the specific wavelength range of the fourth example is a wavelength range of 390 nm or more and 470 nm or less. Note that observation of fluorescence may be referred to as fluorescence observation.

Fifth Modification

A fifth example of the specific wavelength range is a wavelength range of infrared light. The wavelength range of this fifth example includes a wavelength range of 790 nm or more and 820 nm or less or a wavelength range of 905 nm or more and 970 nm or less, and the light of the fifth example has a peak wavelength in the wavelength range of 790 nm or more and 820 nm or less or the wavelength range of 905 nm or more and 970 nm or less.

Generation Example of Special-Light Image

The processor device 12 may generate a special-light image having information in the specific wavelength range on the basis of a normal-light image obtained through imaging using white light. Note that the term "generation" used herein includes "acquisition". In this case, the processor device 12 functions as a special-light image acquisition unit. The processor device 12 obtains a signal of the specific wavelength range by performing calculation based on color information of red, green, and blue or color information of cyan, magenta, and yellow included in the normal-light image.

Note that red, green, and blue are sometimes referred to as RGB. In addition, cyan, magenta, and yellow are sometimes referred to as CMY.

Generation Example of Feature-Quantity Image

As the medical image, a feature-quantity image may be generated through calculation based on at least any of a normal-light image obtained by radiating light in the white range or light in a plurality of wavelength ranges as the light in the white range or a special-light image obtained by radiating light in the specific wavelength range.

Application Example to Program for Causing Computer to Function as Image Processing Apparatus The above-described medical image processing method can be configured as a program that implements functions corresponding to respective steps of the medical image processing method using a computer. For example, a program may be configured to cause a computer to implement an image acquisition function of acquiring a medical image, a region-of-interest detection function of detecting a region of interest from the medical image, an emphasis region setting function of setting a location of an emphasis region for emphasizing the region of interest in accordance with a location of the region of interest when the medical image is displayed using a display device, and a display control function of updating display of the emphasis region using an update interval exceeding an update interval of display of the medical image.

The program that causes a computer to implement the above-described image processing functions may be stored on a computer-readable information storage medium which is a non-transitory tangible information storage medium, and the program may be provided via the information storage medium.

In addition, instead of the configuration in which the program is stored on a non-transitory information storage medium and is provided, a configuration in which a program signal is provided via a network may be employed.

Combination of Embodiments, Modifications, Etc.

The constituent elements described in the embodiments above and the constituent elements described in the modifications can be appropriately used in combination, and some of the constituent elements can be replaced.

In the embodiments of the present invention described above, the constituent elements can be appropriately changed, added, or deleted within a scope not departing from the gist of the present invention. The present invention is not limited to the embodiments described above, and various modifications can be made by a person having the ordinary skill in the art within the technical sprit of the present invention.

REFERENCE SIGNS LIST 9 endoscope system
10 endoscope 11 light source device
12 processor device
13 display device
14 medical image processing apparatus
15 input device
16 monitor device
20 insertion section
21 operation section
22 universal cord
25 soft part
26 bending part
27 tip part
27a tip surface
28 imaging element
29 bending operation knob
30 air/water supply button
31 suction button
32 still image capturing instruction part
33 treatment tool introduction port
35 light guide
36 signal cable
37a connector
37b connector
38 endoscopic image
38a moving image
38b frame image
$38b_1$ frame image
$38b_2$ frame image
$38b_3$ frame image
$38b_4$ frame image
$38b_5$ frame image
$38b_6$ frame image
$38b_7$ frame image
$38b_8$ frame image
39 still image
40 image acquisition unit
41 region-of-interest detection unit
42 emphasis region setting unit
43 update interval setting unit
44 display control unit
46 storage unit
47 endoscopic image storage unit
48 region-of-interest storage unit
49 emphasis region storage unit
120 control unit
122 memory
124 storage device
126 network controller
128 power supply device
130 display controller
132 input/output interface
134 input controller
136 bus
140 network
150 region of interest
150a region of interest
150b region of interest
152 emphasis region
152a emphasis region
152b emphasis region
154 center of gravity
154a center of gravity
154b center of gravity
214 medical image processing apparatus
220 discrimination unit
243 update interval setting unit
246 storage unit
250 discrimination result storage unit
314 medical image processing apparatus
320 endoscope information acquisition unit
343 update interval setting unit
346 storage unit
350 endoscope information storage unit
1501 region of interest
1502 region of interest
1503 region of interest
1507 region of interest
1521 emphasis region
1522 emphasis region
1523 emphasis region
1527 emphasis region
1541 center of gravity
1542 center of gravity
1543 center of gravity
1547 center of gravity
S10 to S24 steps of medical image processing method

What is claimed is:

1. A medical image processing apparatus comprising one or more processors configured to:
acquire a plurality of medical images comprising a first medical image and a second medical image;
detect a region of interest from each of the medical images and identify a location of the region of interest in each of the medical images;
set a location of an emphasis region on each of the medical images for emphasizing the region of interest in accordance with the location of the region of interest, wherein the emphasis region comprises a frame enclosing the region of interest;
display, on the first medical image, a first emphasis region enclosing the region of interest detected from the first medical image using a monitor; and
update display of the emphasis region superimposed on the first medical image using an update interval exceeding an update interval of display of each of the medical images, wherein the one or more processors are further configured to:
calculate a location of a second emphasis region enclosing the region of interest detected in the second medical image by averaging locations of emphasize regions set on the medical images; and
display, on the second medical image, the second emphasis region enclosing the region of interest detected from the second medical image using the monitor.

2. The medical image processing apparatus according to claim 1, wherein the one or more processors are further configured to:
set the update interval of the emphasis region.

3. The medical image processing apparatus according to claim 2, wherein the one or more processors are further configured to:
receive a signal indicating the update interval of the emphasis region, the signal being transmitted from outside; and
set the update interval of the emphasis region on the basis of the received signal indicating the update interval of the emphasis region.

4. The medical image processing apparatus according to claim 2, wherein the one or more processors are configured to set the update interval of the emphasis region in accordance with a movement of an imaging apparatus that acquires the medical images.

5. The medical image processing apparatus according to claim 2, wherein the one or more processors are configured to set the update interval of the emphasis region in accordance with a discrimination result of the region of interest.

6. The medical image processing apparatus according to claim 1, wherein the one or more processors are configured to cause the monitor to display the emphasis region while maintaining, for a period from an update timing of the display of the emphasis region to a next update timing of the display of the emphasis region, the location of the emphasis region at the update timing of the display of the emphasis region.

7. The medical image processing apparatus according to claim 1, wherein the one or more processors are configured to transmit, to the monitor, a signal for displaying the emphasis region to be superimposed on the first medical image.

8. The medical image processing apparatus according to claim 1, wherein the one or more processors are configured to set the location of the emphasis region in a frame at an update timing of the emphasis region on the basis of locations of the regions of interest in two or more frames preceding the frame at the update timing of the emphasis region.

9. The medical image processing apparatus according to claim 8, wherein the one or more processors are configured to set the location of the emphasis region in the frame at the update timing of the emphasis region on the basis of an average of the locations of the regions of interest in the two or more frames preceding the frame at the update timing of the emphasis region.

10. The medical image processing apparatus according to claim 1, wherein the one or more processors are configured to, at an update timing of the display of the emphasis region, set an emphasis region obtained by merging an emphasis region in a past frame with the emphasis region at the update timing of the display of the emphasis region.

11. The medical image processing apparatus according to claim 1, wherein the location of the emphasis region on each of the medical images represents coordinate values of center of gravity of the emphasis region.

12. The medical image processing apparatus according to claim 1, wherein
the medical images are time-series medical images, and
wherein the second medical image is not adjacent to the first medical image.

13. An endoscope system comprising one or more processors configured to:
control an endoscope;
acquire a plurality of medical images comprising a first medical image and a second medical image from the endoscope;
detect a region of interest from each of the medical images and identify a location of the region of interest in each of the medical images;
set a location of an emphasis region on each of the medical images for emphasizing the region of interest in accordance with the location of the region of interest, wherein the emphasis region comprises a frame enclosing the region of interest;
display, on the first medical image, a first emphasis region enclosing the region of interest detected from the first medical image using a monitor; and
update display of the emphasis region superimposed on the first medical image using an update interval exceeding an update interval of display of each of the medical images, wherein the one or more processors are further configured to:
calculate a location of a second emphasis region enclosing the region of interest detected in the second medical image by averaging locations of emphasize regions set on the medical images; and
display, on the second medical image, the second emphasis region enclosing the region of interest detected from the second medical image using the monitor.

14. A medical image processing method comprising:
acquiring a plurality of medical images comprising a first medical image and a second medical image;
detecting a region of interest from each of the medical images and identify a location of the region of interest in each of the medical images;
setting a location of an emphasis region on each of the medical images for emphasizing the region of interest in accordance with the location of the region of interest, wherein the emphasis region comprises a frame enclosing the region of interest;
displaying, on the first medical image, a first emphasis region enclosing the region of interest detected from the first medical image using a monitor; and
updating display of the emphasis region superimposed on the first medical image using an update interval exceeding an update interval of display of each of the medical images, wherein the updating display of the emphasis region comprises:
calculating a location of a second emphasis region enclosing the region of interest detected in the second medical image by averaging locations of emphasize regions set on the medical images; and
displaying, on the second medical image, the second emphasis region enclosing the region of interest detected from the second medical image using the monitor.

15. A non-transitory computer-readable storage medium storing instructions that, when read by a computer, cause the computer to:
acquire a plurality of medical images comprising a first medical image and a second medical image;
detect a region of interest from each of the medical images and identify a location of the region of interest in each of the medical images;
set a location of an emphasis region on each of the medical images for emphasizing the region of interest in accordance with the location of the region of interest, wherein the emphasis region comprises a frame enclosing the region of interest;
display, on the first medical image, a first emphasis region enclosing the region of interest detected from the first medical image using a monitor; and
update display of the emphasis region superimposed on the first medical image using an update interval exceeding an update interval of display of each of the medical images, wherein the computer is further configured to:
calculate a location of a second emphasis region enclosing the region of interest detected in the second medical image by averaging locations of emphasize regions set on the medical images; and
display, on the second medical image, the second emphasis region enclosing the region of interest detected from the second medical image using the monitor.

* * * * *